United States Patent
Nishida et al.

(10) Patent No.: US 8,137,943 B2
(45) Date of Patent: Mar. 20, 2012

(54) HEAT-RESISTANT DNA LIGASE WITH HIGH REACTIVITY

(75) Inventors: Hirokazu Nishida, Kokubunji (JP); Maiko Tanabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 326 days.

(21) Appl. No.: 12/390,767

(22) Filed: Feb. 23, 2009

(65) Prior Publication Data

US 2011/0053147 A1    Mar. 3, 2011

(51) Int. Cl.
- *C12N 9/00* (2006.01)
- *C07K 1/00* (2006.01)
- *C07H 21/04* (2006.01)

(52) U.S. Cl. .................. 435/183; 530/350; 536/23.2

(58) Field of Classification Search .................. None
See application file for complete search history.

(56) References Cited

U.S. PATENT DOCUMENTS

2009/0061481 A1* 3/2009 Nishida et al. ............... 435/69.1

FOREIGN PATENT DOCUMENTS

JP    2008-245604    10/2008

OTHER PUBLICATIONS

UniProt Accession No. Q02093,DNA ligase, created on Apr. 1, 1993).*
"Development of the World's Most Thermostable Enzyem (DNA Ligase) for Gene Diagnosis", http://www.aist.go.jp/aist_j/press_release/pr2003/pr20030910.html.
"A Novel ADP-dependent DNA Ligase From Aeropyrum Pernix K1" Sung-Jong Jeon, et al.
Sung-Jong Jeon, "A Novel ADP-dependent DNA Ligase From Aeropyrum Pernix K1", FEBS Letters 550 (2003), pp. 69-73.

* cited by examiner

*Primary Examiner* — Anand Desai
*Assistant Examiner* — Iqbal H Chowdhury
(74) *Attorney, Agent, or Firm* — Mattingly & Malur, PC

(57) ABSTRACT

Thermostable DNA ligases with enhanced DNA binding activity and reaction activity are obtained. These modified thermostable DNA ligases having enhanced DNA binding activity compared to the wild type can be obtained by substituting a negatively charged amino acid (for example, the amino acid corresponding to the aspartic acid at position 540 of SEQ ID NO: 1) present at the N-terminal side of the C-terminal helix moiety of thermostable DNA ligases from thermophilic bacteria, hyperthermophilic bacteria, thermophilic archaea, or hyperthermophilic archaea, with a non-negatively charged amino acid (for example, alanine, serine, arginine, or lysine).

8 Claims, 2 Drawing Sheets

FIG. 2

|  |  |  | Motif VI |  |
|---|---|---|---|---|
| Archaea | (Crenarchaeota) | | | |
| (SEQ ID NO. 24) Pae 502 | HRHPRVVSK--MEADVWFVPQVVIEVIGAEITLSPLHTCCLGAVRPGVGLAV | RFPRFTGRYRSDKSPEQATTVAEMLELYKRQKKVVQPE | ------ | 589 |
| (SEQ ID NO. 25) Dam 509 | TPHPRVVST--MVPDVWLTPALVAEIIGAEITISPLHTCKDQYAEGG-LSI | RFPRFIR-WRPDKSPEDATTNREILEMYKSQLKKIEEKPSDQSV | ------ | 600 |

Archaea (Euryarchaeota)
(SEQ ID NO. 26) Afu 488 QQGK----------KVEFIPKYVFEVAYQEIQKSPKYESG----------YAL RFPRFVR-LRDDKDVDEADTIERV-ENLYKLQFEVKRQ---------- 556
(SEQ ID NO. 27) Mth 493 RKGR----------KLLVRPEIILEVAYSEIVKSPEYESG----------YSL RFPVVKR-IRDDLCLDDVDTVGRI-ESLFQSGQPDQPG---------- 561
(SEQ ID NO. 28) Mja 507 DLGE----------EVEVPKIVIEVAVEEIQKSDKYPCG----------YAL RFPRVVR-FRFDKGVMEINTIEDV-ERIYEIQRGR-K---------- 573
(SEQ ID NO. 29) Tko 493 QEGK----------FVEIEPKFVIEVTYQEIQKSPKYKSG----------FAL RFPRYVA-LREDKSPEEADTIERVAEL YELQERFKAKK---------- 562
(SEQ ID NO. 30) Pab 490 EEGK----------RVWIQPKVVIEVTYQEIQKSPKYRSG----------FAL RFPRYVA-LREDKGPEDADTIERIAQL YELQERMKGKV---------- 559
(SEQ ID NO. 31) Pfu 490 EEGK----------RVWLQPKVVIEVTYQEIQKSPKYRSG----------FAL RFPRFVA-LRDDKGPEDADTIERIAQL YELQEKMKGKVES-------- 561

Eukarva
(SEQ ID NO. 32) huL 819 SPRPYVRIDGAVIPDHWLDPSAMWEVKCADLSLSPIYPAARGLVDSDKGISL RFPRFIR-VREDKQPEQATTSAQVACL YRKQSQIQNQGEDSGSDPEDTY 919
(SEQ ID NO. 33) Sc1 671 GPKATFVFDSSAEPDVWFEPTTLFEVLTADLSLSPIYKAGSATFDKG--VSL RFPRFLR-IREDKGVEDATSSDQIVEL YENQSHMQN----------- 755

Pae, Pyrobaculum aerophilum (U82370)
Dam, Desufurolobus ambivalens (Q02093)
Afu, Archaeglobus fulgidus (O29632)
Mth, Methanobacterium thermoautotrophicum (U51624-4)
Mja, Methanococcus jannaschii (U67474-4)
Tko, Thermococcus kodakaraensis (AB042527)
Pab, Pyrococcus abyssi (B75173)
Pfu, Pyrococcus furiosus (NC003413 - complete genome - )
huL, Homo sapiens
ScL, Saccharomyces cerevisiae (Z74212-1)

HEAT-RESISTANT DNA LIGASE WITH HIGH REACTIVITY

SEQUENCE LISTING

The instant application contains a Sequence Listing which has been submitted in ASCII format via EFS-Web and is hereby incorporated by reference in its entirety. Said ASCII copy, created on Aug. 26, 2011, is named H&A6986.txt and is 76,764 bytes in size.

BACKGROUND OF THE INVENTION

1. Field of the Invention

The present invention relates to variant DNA ligases. In particular, the invention relates to modified thermostable DNA ligases having higher DNA binding activity and enhanced reaction activity compared to the wild type, which can be obtained by substitution of a negatively charged amino acid present at the N-terminal side of the C-terminal helix moiety of the DNA ligase with a non-negatively charged amid acid, the DNA encoding the modified thermostable DNA ligases, and the use of such modified thermostable DNA ligases, and the like.

2. Background Art

DNA ligase is an enzyme having activity that links a 3'-hydroxyl group of a DNA chain to a 5'-phosphate group of a DNA chain via a phosphodiester bond, and plays a role in replication and repair of DNA in vivo. In recent years, the ligase chain reaction (LCR) method has been developed as a new gene amplification technique, and used. The LCR method is a method of amplifying or detecting a target gene through a thermal cycling reaction using a thermostable DNA ligase. Ligases with improved thermostability have been sought for improving the efficiency of LCR method, and some are commercially available. Very recently, a DNA ligase from a hyperthermophilic archaeon has been found (as described in Non-Patent Document 1). However, these thermostable DNA ligases have a very low DNA binding activity. DNA ligases from phages are known as enzymes with high DNA binding activity. But they are not suited for use in the LCR method because of their poor thermostability. Thus, a thermostable DNA ligase with good DNA binding activity and reactivity, with which the LCR method can be carried out efficiently at a satisfactory reaction rate, has not yet been found.

[Non-Patent Document 1]: "Successful development of a genetic diagnostic enzyme (DNA ligase) having the highest known thermal stability", Press release on the website of the National Institute of Advanced Industrial Science and Technology (2003)

SUMMARY OF THE INVENTION

Problems to be Solved

The problem to be solved by the invention is to provide a thermostable DNA ligase having high DNA binding activity and enhanced reaction activity.

Means for Solving the Problems

After painstaking investigations undertaken to solve the aforementioned problem, the present inventors found that the C-terminal helix moiety of DNA ligase inhibited the flexibility of the enzyme, resulting in suppression of its DNA binding activity. Subsequently, the present inventors succeeded in enhancing the DNA binding activity by truncating a part or whole of the C-terminal helix. However, this DNA ligase still had the problem of low stability, although its DNA binding activity had enhanced. This problem may be caused by a charged amino acid(s) behind the C-terminal helix moiety getting exposed on the surface of the protein due to the truncation in the C-terminal, which results in decrease of the hydrophilicity of the enzyme. The present inventors found that a DNA ligase with high reaction efficiency can be obtained if some or all of the charged amino acids present in the C-terminal helix are substituted with hydrophilic amino acids having small side chains (alanine, threonine, and serine).

Furthermore, the present inventors found that a common mutation site (the aspartic acid at position 540) of the variants having enhanced reaction activity plays an important role in enhancing reaction activity, prepared variants in which this site was substituted with various amino acids, and successfully created a variant with a hitherto unknown high level of reaction activity. This led to the perfection of the present invention.

Thus, the present invention provides a modified thermostable DNA ligase having higher DNA binding activity compared to the wild type, which can be obtained by substituting the negatively charged amino acid(s) present at the N-terminal side (the region corresponding to positions 536 to 541 in SEQ ID NO: 2) of the C-terminal helix moiety of thermostable DNA ligases from thermophilic bacteria, hyperthermophilic bacteria, thermophilic archaea, or hyperthermophilic archaea with non-negatively charged amino acid(s).

As for the negatively charged amino acid present at the N-terminal side of the C-terminal helix moiety to be modified, an amino acid exposed on the surface of the protein is preferable, and it may include, for example, a negatively charged amino acid in the amino acid sequence of the thermostable DNA ligase, which corresponds to the aspartic acid at position 540 of the amino acid sequence of the thermostable DNA ligase from *Pyrococcus furiosus* shown in SEQ ID NO: 2, when the amino acid sequence of the thermostable DNA ligase is aligned with the aforementioned amino acid sequence of SEQ ID NO: 2.

Any amino acid can be used for the substitution as long as it is non-negatively charged, as mentioned above, and such amino acids include non-charged amino acids (alanine, glycine, valine, leucine, isoleucine, phenylalanine, methionine, tryptophane, cysteine, serine, asparagine, glutamine, threonine, and tyrosine), and positively charged amino acids (arginine, lysine, and histidine). Among these, substitution with a positively charged amino acid (arginine or lysine) is preferable.

Suitable examples of the enzyme may include a thermostable DNA ligase from *Pyrococcus furiosus*.

Specific examples of modified thermostable DNA ligase of the present invention may include modified thermostable DNA ligases obtained by substituting the aspartic acid at position 540 of the thermostable DNA ligase from *Pyrococcus furiosus* shown in SEQ ID NO: 2 with alanine, serine, arginine, or lysine.

The present invention also provides DNA encoding the aforementioned modified thermostable DNA ligase, and expression vectors comprising the DNA.

The invention further provides a method of producing a modified thermostable DNA ligases, comprising culturing a host cell wherein the aforementioned vector has been introduced and harvesting the protein having DNA ligase activity from the culture.

The present invention further provides an LCR method in which the modified thermostable DNA ligase of the present invention is used, and LCR kit therefor.

Effects Achieved by the Present Invention

The present invention provides modified thermostable DNA ligases that have superior DNA binding activity (binding capacity) and reaction activity (stability) than in the native state. According to the modified thermostable DNA ligases of the present invention, a rapid and highly specific LCR method, and efficient gene amplification and detection of point mutations can be accomplished. Also, highly selective gene engineering is possible using the modified thermostable DNA ligases of the present invention.

BRIEF DESCRIPTION OF THE DRAWINGS

FIG. 2 shows the alignment of different DNA ligases.

DETAILED DESCRIPTION OF THE EMBODIMENTS

1. Modified Thermostable DNA Ligases

Figure 1:
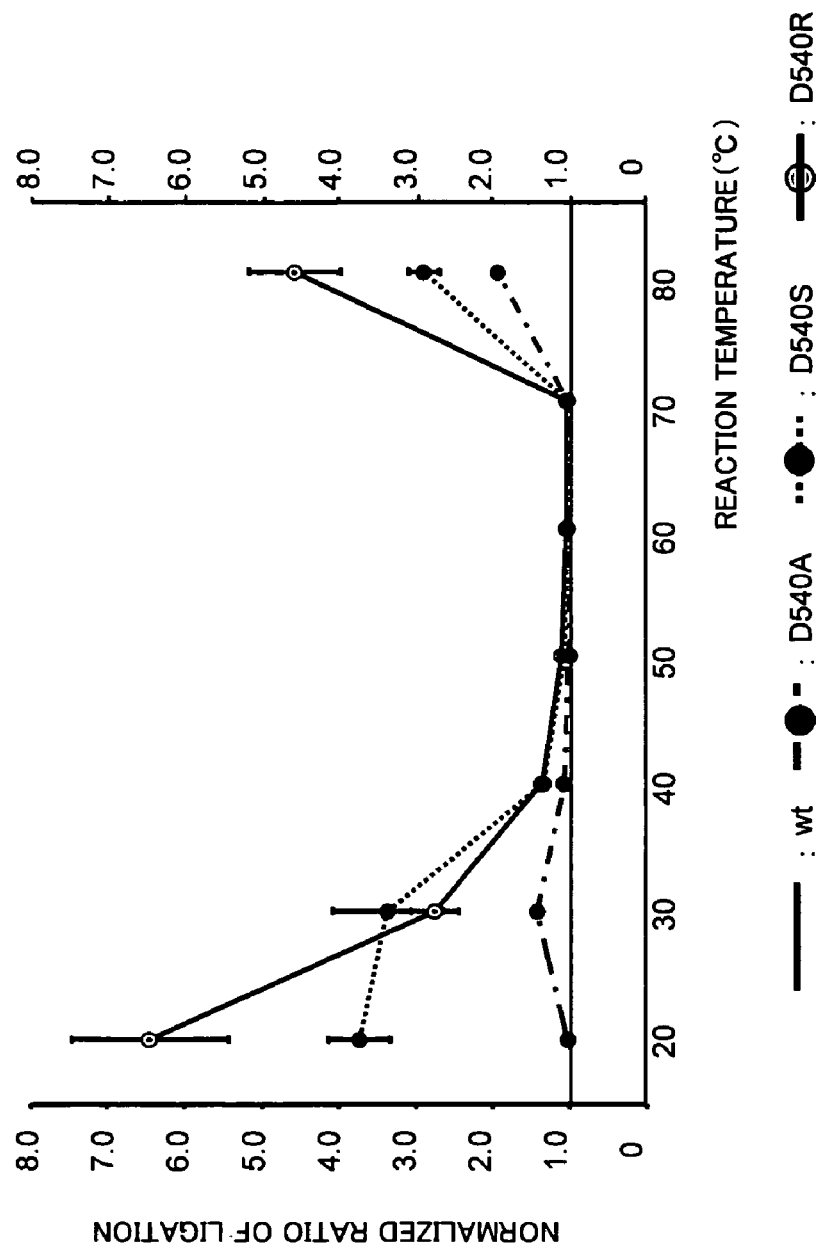
FIG. 1 is a graph showing specific activity, at different temperatures, of DNA ligases (D540A, D540S, and D540R) wherein a mutation has been introduced at the aspartic acid at position 540, when the reaction activity of wild type DNA ligase is taken as 1.

The present invention relates to modified thermostable DNA ligases having superior DNA binding activity and reactivity (stability) than the wild type (native) enzyme, which can be obtained by substituting at least two charged amino acids present in the C-terminal helix moiety of a thermostable DNA ligase from thermophilic bacteria, hyperthermophilic bacteria, thermophilic archaea, or hyperthermophilic archaea, with alanine, threonine or serine.

"Thermostable DNA ligase" used in the present invention means a DNA ligase with superior thermal stability which may obtained from thermophilic bacteria (such as *Bacillus stearothermophilus*), hyperthermophilic bacteria (such as *Thermotoga maritima*), thermophilic archaea (such as *Thermoplasma volcanium*), or hyperthermophilic archaea (such as *Aeropyrum pernix*). The amino acid sequences of these thermostable ligases are already known, and are registered in public databases such as GenBank: *Archaeglobus fulgidus* (O29632), *Methanobacterium thermoautotrophicum* (U51624-4), *Methanococcus jannaschii* (U67474-4), *Thermococcus kodakaraensis* (AB042527), *Pyrococcus abyssi* (B75173), and *Pyrococcus furiosus* (NC003413—complete genome—). Among the aforementioned thermostable DNA ligases, those from hyperthermophilic bacteria or hyperthermophilic archaea are preferable. One example of the most preferable may include a DNA ligase (SEQ ID NO: 2) from *Pyrococcus furiosus*.

Normal DNA ligases act at 20 to 30° C., but the DNA ligases of the aforementioned bacteria can maintain stable activity even at high temperatures, and therefore, are very useful for nucleic acid amplification techniques like LCR and genetic engineering techniques that require thermal cycling. It is preferable for the DNA ligases of the present invention to be able to maintain enzymatic activity at 70° C. or higher, especially at 90° C. or higher, but not limited thereto.

The thermostable DNA ligase of the present invention has a helix moiety at the C-terminus and sequence homology (60% or higher, preferably 70% or higher, and more preferably 80% or higher, at the amino acid sequence level) with the DNA ligase from *Pyrococcus furiosus* (SEQ ID NO: 2). Here, "helix moiety" means the continuous amino acid region that constitutes the helix of the enzyme. Many DNA ligases have a helix moiety at the C-terminus, and DNA ligases from humans, yeast, and bacteria also have the helix at the C-terminus. The C-terminal helix moiety is believed to strengthen the structure of the enzyme. But on the other hand, it inhibits the enzyme's flexibility, which reduces its DNA binding activity, and becomes a cause of lowering of the reactivity.

According to the present invention, the DNA binding activity and reactivity are enhanced by substituting negatively charged amino acid(s) (glutamic acid, aspartic acid) present near the N-terminal side of the C-terminal helix moiety, with non-negatively charged amino acid(s). Here, "near the N-terminal side of the C-terminal helix moiety" refers to, in the DNA ligase (SEQ ID NO: 2) from *Pyrococcus furiosus* as an example, the part corresponding to the amino acids at positions 536 to 541.

The amino acid used for the substitution can be any amino acid as long as it is a non-negatively charged amino acid, and may include non-charged amino acids (alanine, glycine, valine, leucine, isoleucine, phenylalanine, methionine, tryptophane, cysteine, serine, asparagine, glutamine, threonine and tyrosine) and positively charged amino acids (arginine, lysine, and histidine). It is preferable to substitute with an amino acid having a positively charged amino acid (arginine or lysine).

More specifically, the amino acid in the amino acid sequence of the thermostable DNA ligase of interest, which corresponds to the aspartic acid at position 540 of the amino acid sequence of the thermostable DNA ligase from *Pyrococcus furiosus* shown in SEQ ID NO: 2, when it is aligned with the amino acid sequence shown in SEQ ID NO: 2, is substituted as described above. FIG. 2 shows examples of such alignment. In FIG. 2, Motif VI is one of the 6 portions (motifs I to VI), common to all DNA ligases, having a particularly high homology. A sequence closer to this motif is easier to assess the homology in the alignment. The C-terminal helix moiety modified according to the present invention is very close to Motif VI.

The aforementioned amino acid substitution can be achieved by a method known to persons skilled in the art. For example, it can be achieved by substituting the amino acid codon of interest with the mutation-introducing amino acid codon, using site-directed mutagenesis.

The DNA ligase thus obtained has high DNA binding activity not only at about 20 to 30° C., the normal reactive range of the enzyme, but also at the high temperature of 70 to 80° C., and thus has higher reaction activity than the wild type. The DNA ligase preferably has 1.5 to 6 times the binding activity (ligation efficiency) of the wild type, particularly 5 to 6 times at 20° C. and 4 to 5 times at 80° C., compared to the corresponding wild type. The modified thermostable DNA ligase of the present invention is useful in nucleic acid amplification techniques and genetic engineering techniques that require thermal cycling.

2. Recombinant Production of Modified Thermostable DNA Ligase 2.1 DNA Encoding Modified Thermostable DNA Ligases DNA encoding the modified thermostable DNA ligase according to the present invention can be obtained by introducing a site-directed mutation or a site-directed mutation and a stop codon to truncate C-terminal portion to a known wild type thermostable DNA ligase gene. The site-directed mutation can be introduced easily using a commercially available kit (QuickChange XL Site-Directed Mutagenesis Kit (STRATAGENE), or Transformer™ Site-Directed Mutagenesis Kit (CLONTECH), for example).

2.2 Expression Vectors

Next, an expression vector is prepared by linking (inserting) DNA encoding the modified thermostable DNA ligase into a known vector such as a plasmid. The vector is not particularly limited as long as it can replicate in the host, and may include, for example, plasmid DNA and phage DNA.

Examples of such plasmid DNA include plasmids derived from *Escherichia coli* (for example, pBR322, pBR325, pUC18, pUC119, pTrcHis, and pBlueBacHis, particularly pET21 vector having the powerful T7 promoter being preferable), plasmids derived from *Bacillus subtilis* (for example, pUB110, and pTP5), and plasmids derived from yeasts (for example, YEp13, YEp24, YCp50, and pYE52). Examples of phage DNA include λ phage.

For inserting the gene of the present invention into the vector, the method of firstly cutting the purified DNA using suitable restriction enzymes, and then inserting at suitable restriction enzyme sites or multicloning site of the vector DNA to link it with the vector, is employed.

To express the foreign gene in the host, a suitable promoter has to be placed upstream of the structural gene. The promoter is not particularly limited, and any promoter known to function in the host can be used. The promoter for each host will be discussed in detail below, in relation to the transformants. If necessary, cis elements such as enhancers, splicing signals, poly A-addition signal, ribosomal binding sequence (SD sequence), and terminator sequence, etc. may also be placed.

Examples of plasmids that can be used to express the modified thermostable DNA ligase of the present invention include pET21d-ligD540A, pET21d-ligD540S, and pET21d-ligD540R obtained in the present invention.

2.3 Modified Thermostable DNA Ligase Expression Systems (Host Cells)

Next, an expression system for the modified thermostable DNA ligase is prepared by introducing the aforementioned vector into a host in such a way that a gene of interest is expressed. The host is not particularly limited as long as it can express the DNA of the present invention, and examples may include bacteria belonging to the genus *Escherichia*, such as *E. coli*, the genus *Bacillus*, such as *B. subtilis*, the genus *Pseudomonas*, such as *P. putida*, and the genus *Rhizobium*, such as *R. melioti*; yeasts such as *Saccharomyces cerevisiae*, *Schizosaccharomyces pombe* and *Pichia pastoris*; and also animal cells, such as COS cells and CHO cells, and insect cells, such as Sf19 and Sf21.

When using a bacterium such as *Escherichia coli* as the host, it is preferable that the recombinant vector of the present invention can replicate autonomously in the bacterium, and comprises a promoter, ribosomal binding sequence, the gene of the present invention, and a transcription terminator sequence. The recombinant vector may also contain an element that controls the promoter. Examples of *Escherichia coli* strains include the HMS174(DE3), K12, DH1, and the B strain, and examples of *Bacillus subtilis* strains include MI 114 and 207-21. The promoter is not particularly limited and any promoter that can be expressed in the aforementioned hosts including *Escherichia coli* may be used, and examples include promoters derived from *E. coli* or phage, such as trp promoter, lac promoter, $P_L$ promoter, and $P_R$ promoter. Furthermore, artificially designed and engineered promoters such as tac promoter can be used. A method of introducing the recombinant vector into the bacterium is not particularly limited, and may include a method that uses calcium ions [Cohen, S. N. et al.: Proc. Natl. Acad. Sci., USA, 69: 2110-2114 (1972)], and electroporation.

As yeast host, *Saccharomyces cerevisiae*, *Schizosaccharomyces pombe* or *Pichia pastoris* may be used, for example. The promoter is not particularly limited as long as it can be expressed in the yeast, and examples of promoters can include gal1 promoter, gal10 promoter, heat shock protein promoter, MFα1 promoter, PHO5 promoter, PGK promoter, GAP promoter, ADH promoter, and AOX1 promoter. A method of introducing the vector into the yeast is not particularly limited, and may include electroporation [Becker, D. M. et al.: Methods. Enzymol., 194: 182-187 (1990)], spheroplast method [Hinnen, A. et al.: Proc. Natl. Acad. Sci., USA, 75: 1929-1933 (1978)], and lithium acetate method [Itoh, H.: J. Bacteriol., 153: 163-168 (1983)].

2.4 Culturing of the Transformant

The modified thermostable DNA ligase of the present invention can be obtained by culturing the above-described transformant in a suitable medium and harvesting the protein having DNA ligase activity from the culture. The method of culturing the transformant of the present invention is suitably selected, depending on the host. For example, in the case of transformants where a microorganism such as *Escherichia coli* or yeast is the host, either a natural or a synthetic medium can be used as long as the medium contains a carbon source, nitrogen source, inorganic salts, etc. that the microorganism can utilize, and the transformant can be efficiently cultured in it.

During the culture, antibiotics such as ampicillin and tetracycline may be added to the medium, if needed. An inducer may be added to the medium, if necessary, when culturing a microorganism that has been transformed using an expression vector in which an inducible promoter is used. For example, when culturing a microorganism transformed with an expression vector in which lac promoter has been used, isopropyl-β-thiogalactopyranoside (IPTG), etc. may be added to the medium, and when culturing a microorganism transformed with an expression vector in which trp promoter has been used, indoleacrylic acid (IAA), etc. may be added.

After culturing, the bacteria or cells are disrupted if the enzyme protein of the present invention is produced therein. On the other hand, if the protein of the present invention is secreted outside the bacteria or cells, the culture fluid without treatment may be used, or the protein can be recovered by centrifugation, etc.

For isolating and purifying the protein, ammonium sulfate precipitation, SDS-PAGE, gel filtration, ion exchange chromatography, affinity chromatography, etc. may be used singly or in suitable combinations.

The enzymatic activity of the modified thermostable DNA ligase of the present invention can be confirmed by detecting ligation using fluorescence, and the like, by the method described in the examples. Alternatively, an antibody that specifically binds with the desired modified thermostable DNA ligase may be prepared, and its expression can also be examined by western blotting, using the antibody.

3. LCR that Uses the Modified Thermostable Ligase, and an LCR Kit

In another aspect, the present invention provides an LCR method that uses the modified thermostable DNA ligase of the present invention and an LCR kit comprising the modified thermostable ligase of the present invention. As described above, the modified thermostable DNA ligase of the present invention retains high enzymatic activity even at high temperature and may exhibit its effectiveness in the LCR method, which requires thermal cycling. Thus, a rapid and highly specific LCR method and efficient gene amplification, detection of point mutations, etc. can be carried out using the modified thermostable ligase of the present invention having superior thermostability and superior DNA binding activity and reactivity.

The LCR kit of the present invention comprises the modified thermostable ligase of the present invention as an essential component. The kit may additionally comprise an instruction, and reagents and tools normally needed for LCR, such as surfactant, dNTPs (nucleic acids), various primers (nucleic acids), pH buffer, magnesium solution, and cofactors like other peptides or proteins.

EXAMPLES

The present invention is described more specifically below referring some examples. However, these examples may not be intended to limit the scope of the present invention.

Example 1

Preparation of Ligase with Mutation Introduced in the C-Terminal Helix (1) Preparation of *Pyrococcus furiosus* Genomic DNA

*P. furiosus* DSM3638 was obtained from Deutsche Sammlung von Mikroorganismen and Zelkulturen GmbH, and cultured following the method described in the literature (Nucleic Acids Research, Vol. 21, 259-265). About 1.2 g of the bacteria was obtained from 500 ml of the culture medium. These bacteria were suspended in 10 ml of Buffer L (10 mM tris-hydrochloric acid (pH 8.0), 1 mM EDTA, 100 mM NaCl), and 1 ml of 10% SDS was added thereto. After stirring, 50 ml of proteinase K (20 mg/ml) was added and the suspension was left standing for 60 minutes at 55° C. The reaction mixture was then extracted sequentially, first with phenol, then phenol-chloroform, and finally with chloroform. Then ethanol was added to produce insoluble DNA. The DNA recovered was dissolved in 1 ml of TE solution (10 mM tris-hydrochloric acid (pH 8.0), and 1 mM EDTA), and 0.75 mg RNase A was added and the reaction allowed to occur for 60 minutes at 37° C. Then, the reaction mixture was once again extracted with phenol, phenol-chloroform, and chloroform. After that, the DNA was recovered by ethanol precipitation to obtain 0.75 mg of DNA.

(2) Cloning of Lig Gene

We designed primers for amplifying, through PCR, a region of the genomic DNA of *P. furiosus* predicted to be lig gene. 5'-CTAGTGGATCTGATGCGTTATCTGG-3' (SEQ ID NO: 11) and 5'-TCGGGACTATTGTTAGACCTTAGC-3' (SEQ ID NO: 12) were synthesized as the primers for the first PCR. As the primers to be used in the 2nd PCR, 5'-GGC-CATGGGTTATCTGGAGCTTGCTCAAC-3' (SEQ ID NO: 13) and, 5'-GCGGATCCTTAGCTTTC-CACTTTTCTTTCATC-3' (SEQ ID NO: 14) were prepared in such a way that each would get annealed inner side than the respective first primers. The NcoI recognition sequence was incorporated in the forward primer to be in-frame with ATG, predicted to be the translation start codon of lig gene. As for the reverse primers, the BamHI recognition sequence was introduced immediately after the stop codon. The gene of interest was amplified using PyroBEST DNA polymerase (Takara Bio Inc) under the PCR conditions consisting of thermal denaturing at 95° C., annealing at 55° C., and extension reaction at 72° C. for 30 cycles. The 2nd PCR was carried out using the product of the first PCR as the template, under the same conditions, and the product was incorporated into pGEM-T easy vector (Promega Corp), and the nucleotide sequence of the fragment-inserted region was confirmed with a DNA sequencer (Beckman Coulter). Then, cutting was done at NcoI-BamHI, and lig gene cut out from the pGEM-T easy vector was inserted into pET21d vector (EMD Bio-Science) to obtain pET21d-lig plasmid. To construct this expression system, the NcoI sequence was introduced at the site of the start codon. Because of that, the second codon AGG in the sequence shown in the SEQ ID NO: 1 was changed to GGT, and the second amino acid in the translation product to be obtained, which was originally arginine, was glycine (see SEQ ID NOs: 3 and 4).

To prepare a variant (D540A), where the aspartic acid at position 540 is substituted with alanine, using the plasmid pET21d-lig as the template, the mutation was introduced by site-directed mutagenesis through the procedure described below. The gene of interest was amplified using the primer set of 5'-GGACCAGAAGATGCAGCTACAATAGAGAGA-3' (SEQ ID NO: 15) and 5'-TCTCTCTATTGTAGCTGCATCT-TCTGGTCC-3' (SEQ ID NO: 16) for preparing the variant (D540A) and PyroBEST DNA polymerase (Takara Bio Inc) under the PCR conditions consisting of thermal denaturing at 95° C., annealing at 55° C., and extension reaction at 72° C. for 20 cycles to obtain a desired D540A plasmid (pET21d-ligD540A).

Next, to prepare a variant (D540S), where the aspartic acid at position 540 is substituted with serine, the mutation was introduced by site-directed mutagenesis through the procedure described below. The gene of interest was amplified using the plasmid pET21d-lig as the template, the primer set of 5'-GGACCAGAAGATGCATCTACAATAGAGAGA-3' (SEQ ID NO: 17) and 5'-TCTCTCTATTGTAGATGCATCT-TCTGGTCC-3' (SEQ ID NO: 18) for preparing the variant (D540S) and PyroBEST DNA polymerase (Takara Bio Inc) under the PCR conditions consisting of thermal denaturing at 95° C., annealing at 55° C., and extension reaction at 72° C. for 20 cycles to obtain the desired D540S plasmid (pET21d-ligD540S).

Further, to prepare a variant (D540R), where the aspartic acid at position 540 is substituted with arginine, the mutation was introduced by site-directed mutagenesis through the procedure described below. The gene of interest was amplified using the plasmid pET21d-lig as the template, the primer set of 5'-GGACCAGAAGATGCACGTACAATAGAGAGA-3' (SEQ ID NO: 19) and 5'-TCTCTCTATTGTACGTGCATCT-TCTGGTCC-3' (SEQ ID NO: 20) for preparing the variant (D540R) and PyroBEST DNA polymerase (Takara Bio Inc) under the PCR conditions consisting of thermal denaturing at 95° C., annealing at 55° C., and extension reaction at 72° C. for 20 cycles to obtain the desired D540R plasmid (pET21d-ligD540R).

(3) Construction of Large-Scale Expression Systems and Purification for the Wild Type Ligase from *P. furiosus* and the Ligases (D540A, D540S, and D540R) Wherein Mutation has been Introduced at the Aspartic Acid at Position 540

Large-scale expression systems for untreated (wild type) ligase and purification thereof are described below. The procedure used was the same for the ligases (D540A, D540S, and D540R) wherein mutation is introduced at the aspartic acid at position 540 except that the plasmid used initially was pET21d-ligD540A, pET21d-ligD540S or pET21d-ligD540R, and similar large-scale expression and purification could be achieved.

The plasmid pET21d-lig, was transformed into BL21 codon plus RIL competent cells (STRATAGENE) and cultured at 37° C. in Luria Bertani medium in the presence of 100 μg·ml⁻¹ ampicillin and 20 μg·ml⁻¹ chloramphenicol. At the point when the culture turbidity (absorbance at 660 nm) reached 0.6, isopropyl-β-D-thiogalactopyranoside was added to a final concentration of 1 mM to induce protein expression. After culturing for further 6 h, the bacteria were recovered by a centrifuge. The bacteria were then suspended in tris-hydrochloric acid buffer (pH 8), sonicated, and centrifuged. The supernatant was heat-treated for 20 min at 80° C. and centrifuged. Polyethyleneimine was added to the supernatant to a final concentration of 0.15% (w/v) and the nucleic acid component was removed by centrifuging. After adding ammonium sulfate to the solution to 80% saturation, it was centrifuged and the precipitate was collected.

The precipitate was dissolved in tris-hydrochloric acid buffer (pH 8) and separated using affinity chromatography (HiTrap Heparin, 5 ml; Amersham Pharmacia Biotech Inc), and the fraction eluted at NaCl concentration 0.4 to 0.5 M was collected. This fraction was further subjected to anion exchange chromatography (HiTrap Q, 5 ml; Amersham Pharmacia Biotech Inc) for separation, and the flow-through fraction was collected. This solution was concentrated and subjected to separation using a gel filtration column (Superdex 200 HiLoad 26/60, Amersham Pharmacia Biotech Inc) at the flow rate of 2 ml/min, and the main peak that was eluted in approximately 100 min was collected. Electrophoresis of this solution confirmed that it was protein of 99% or higher purity. Thus, it shows that variant DNA ligases of the present invention can be obtained easily as described above.

The nucleotide sequence of DNA encoding wild type *Pyrococcus furiosus* DNA ligase is shown in SEQ ID NO: 1, and the amino acid sequence of the protein coded thereby is shown in SEQ ID NO: 2. The C-terminal helix of *P. furiosus* DNA ligase comprises the amino acids 540 (Asp) to 560 (Ser) of the amino acid sequence of SEQ ID NO: 22. The DNA nucleotide sequence encoding the wild type DNA obtained in Example 1 is shown in SEQ ID NO: 3, and the amino acid sequence of the protein encoded thereby is shown in SEQ ID NO: 4. The nucleotide sequence encoding the variant D540A obtained in Example 1 is shown in SEQ ID NO: 5, and the amino acid sequence of the protein encoded thereby is shown in SEQ ID NO: 6. The nucleotide sequence encoding the variant D540S obtained in Example 1 is shown in SEQ ID NO: 7, and the amino acid sequence of the protein encoded thereby is shown in SEQ ID NO: 8. The nucleotide sequence encoding the variant D540R obtained in Example 1 is shown in SEQ ID NO: 9, and the amino acid sequence of the protein encoded thereby is shown in SEQ ID NO: 10.

Example 2

Comparison of the Reaction Activities Between the Wild Type and the Variant DNA Ligases Having Mutation Introduced at the Aspartic Acid at Position 540

(4) The 40 mer oligo DNA (SEQ ID NO: 21) which was the template, the 30 mer oligo DNA (SEQ ID NO: 22) that had been phosphorylated at the 5'-terminus, and the 20 mer oligo DNA (SEQ ID NO: 23) that had been labeled at the 5'-terminus with the fluorescent substance TET were each prepared as 0.5 mM solutions, and an oligo DNA mixture was prepared by mixing 5 μl of each solution. The sequences of the oligo DNAs used are shown in Table 2. The oligo DNA mixture thus prepared was thermally denatured at 95° C. for 5 min. From 94° C., the temperature was lowered to 2° C. at the rate 1° C. per 5 min to hybridize the 3 oligo DNAs and prepare the annealed product. The ligation reaction (13) was carried out using the resultant annealed product as the template. The reaction product was subjected to electrophoresis using 15% acrylamide/8 M urea gel. After the electrophoresis, the TET fluorescence intensities of the two bands corresponding to a 50 mer, the ligation product, and a 20 mer, TET-labeled oligo DNA, were measured using a Fluoroimager 595 (GE) and the image analysis software ImageQuant (Molecular Dynamics). The percentage of the value at 50 mer, when the sum of the fluorescence intensities detected at 50 mer and 20 mer was taken as 100% was defined as the ligation efficiency. The ligation efficiency of each variant ligase was compared by calculating the normalized value of ligation efficiency (ratio of ligation) for each ligase, taking the ligation efficiency of wild type PfuDNA ligase obtained at each temperature as 1.

FIG. 1 shows the normalized ratios of ligation for 3 types of variant ligases and the wild type ligase in reactions in the temperature range 20° C. to 90° C. (the normalized values of the ligation efficiency for the variant ligases when the mean ligation efficiency of the wild type ligase obtained at each reaction temperature was taken as 1). In FIG. 1, the x-axis, the dashed-dotted line, the dotted line, and solid line respectively represent the results obtained with the wild type, D540A, D540S, and D540R.

The above results reveal that, compared to the wild type ligase, D540A had higher ligation efficiency at low temperature (30° C.) and high temperature (80° C.), D540S had higher ligation efficiency at low temperature (20° C. and 30° C.) and high temperature (80° C.), and D540R also had higher ligation efficiency at low temperature (20° C. and 30° C.) and high temperature (80° C.).

Example 3

Thermostability of Variant DNA Ligases of the Present Invention

Both the wild type and the variant DNA ligases used in Example 2 were heat-treated at 85° C. for 20 minutes in the early stage of the purification to intentionally denature the non-thermostable proteins and simplify the subsequent purification procedure. In this heat-treatment, the variants showed thermostability comparable to the native ligase.

INDUSTRIAL APPLICABILITY

The present invention provides modified thermostable DNA ligases having high DNA binding activity and reactivity. Such modified thermostable DNA ligases are useful in nucleic acid amplification techniques such as LCR and genetic engineering techniques, which require reaction at high temperatures. Therefore, the present invention can be used in the fields of biochemical research, research reagents, diagnostic reagents, and pharmaceuticals.

SEQUENCE LISTING FREE TEXT

SEQ ID NO: 1: Wild type DNA ligase from *Pyrococcus furiosus*

SEQ ID NO: 2: Wild type DNA ligase from *Pyrococcus furiosus*

SEQ ID NO: 3: Wild type DNA ligase from *Pyrococcus furiosus* obtained in Example 1

SEQ ID NO: 4: Wild type DNA ligase from *Pyrococcus furiosus* obtained in Example 1

SEQ ID NO: 5: Variant of DNA ligase from *Pyrococcus furiosus* (D540A)

SEQ ID NO: 6: Variant of DNA ligase from *Pyrococcus furiosus* (D540A)

SEQ ID NO: 7: Variant of DNA ligase from *Pyrococcus furiosus* (D540S)
SEQ ID NO: 8: Variant of DNA ligase from *Pyrococcus furiosus* (D540S)
SEQ ID NO: 9: Variant of DNA ligase from *Pyrococcus furiosus* (D540R)
SEQ ID NO: 10: Variant of DNA ligase from *Pyrococcus furiosus* (D540R)
SEQ ID NO: 11: Primer for the 1st PCR of wild type DNA ligase from *Pyrococcus furiosus*
SEQ ID NO: 12: Primer for the 1st PCR of wild type DNA ligase from *Pyrococcus furiosus*
SEQ ID NO: 13: Primer for the 2nd PCR of wild type DNA ligase from *Pyrococcus furiosus*
SEQ ID NO: 14: Primer for the 2nd PCR of wild type DNA ligase from *Pyrococcus furiosus*
SEQ ID NO: 15: Primer for amplification of variant of DNA ligase from *Pyrococcus furiosus* (D540A)
SEQ ID NO: 16: Primer for amplification of variant of DNA ligase from *Pyrococcus furiosus* (D540A)
SEQ ID NO: 17: Primer for amplification of variant of DNA ligase from *Pyrococcus furiosus* (D540S)
SEQ ID NO: 18: Primer for amplification of variant of DNA ligase from *Pyrococcus furiosus* (D540S)
SEQ ID NO: 19: Primer for Amplification of Variant of DNA Ligase from *Pyrococcus furiosus* (D540R)
SEQ ID NO: 20: Primer for amplification of variant of DNA ligase from *Pyrococcus furiosus* (D540R)
SEQ ID NO: 21: 60 mer substrate for DNA ligase from *Pyrococcus furiosus*, and its variants
SEQ ID NO: 22: 30 mer substrate for DNA ligase from *Pyrococcus furiosus*, and its variants
SEQ ID NO: 23: 20 mer substrate for DNA ligase from *Pyrococcus furiosus*, and its variants

What is claimed is:

1. A modified thermostable DNA ligase obtained by substituting a negatively charged amino acid in the amino acid sequence of a thermostable DNA ligase from thermophilic bacteria, hyperthermophilic bacteria, thermophilic archaea, or hyperthermophilic archaea, which corresponds to the aspartic acid at position 540 of the amino acid sequence of the thermostable DNA ligase from *Pyrococcus furiosus* shown in SEQ ID NO: 2, with a non-negatively charged amino acid, when the amino acid sequence of the thermostable DNA ligase is aligned with the amino acid sequence of SEQ ID NO: 2, wherein the thermostable DNA ligase from thermophilic bacteria, hyperthermophilic bacteria, thermophilic archaea, or hyperthermophilic archaea has sequence homology of 80% or higher with the amino acid sequence of SEQ ID NO: 2 and maintains an enzymatic activity at 70° C. or higher.

2. The modified thermostable DNA ligase according to claim 1, wherein the non-negatively charged amino acid is any one selected from alanine, serine, arginine, and lysine.

3. A modified thermostable DNA ligase obtained by substituting the aspartic acid at position 540 of the thermostable DNA ligase from *Pyrococcus furiosus* shown in SEQ ID NO: 2 with a non-negatively charged amino acid.

4. The modified thermostable DNA ligase according to claim 3, wherein the non-negatively charged amino acid is any one selected from alanine, serine, arginine, and lysine.

5. The modified thermostable DNA ligase according to claim 1, wherein the DNA ligase has enhanced DNA binding activity compared to the wild type.

6. A kit for ligase chain reaction (LCR) comprising the modified thermostable DNA ligase according to claim 1.

7. The modified thermostable DNA ligase according to claim 3, wherein the DNA ligase has enhanced DNA binding activity compared to the wild type.

8. A kit for ligase chain reaction (LCR) comprising the modified thermostable DNA ligase according to claim 3.

* * * * *

SEQUENCE LISTING

<160> NUMBER OF SEQ ID NOS: 33

<210> SEQ ID NO 1
<211> LENGTH: 1683
<212> TYPE: DNA
<213> ORGANISM: Pyrococcus furiosus
<220> FEATURE:
<221> NAME/KEY: CDS
<222> LOCATION: (1)..(1683)

<400> SEQUENCE: 1

```
atg agg tat cta gag ctt gct caa ctt tat caa aag tta gaa aag aca     48
Met Arg Tyr Leu Glu Leu Ala Gln Leu Tyr Gln Lys Leu Glu Lys Thr
1               5                   10                  15 act atg aaa ctt ata aag act aga ctt gtc gcc gac ttc ctg aaa aaa     96
Thr Met Lys Leu Ile Lys Thr Arg Leu Val Ala Asp Phe Leu Lys Lys
            20                  25                  30 gta cca gat gat cat ctg gag ttc att ccc tat cta att ctt gga gaa    144
Val Pro Asp Asp His Leu Glu Phe Ile Pro Tyr Leu Ile Leu Gly Glu
        35                  40                  45 gtt ttt cca gag tgg gat gaa agg gag ctg ggt gtg gga gaa aag ctg    192
Val Phe Pro Glu Trp Asp Glu Arg Glu Leu Gly Val Gly Glu Lys Leu
    50                  55                  60 tta att aaa gct gta gca atg gcc act gga att gac gca aaa gaa atc    240
Leu Ile Lys Ala Val Ala Met Ala Thr Gly Ile Asp Ala Lys Glu Ile
65                  70                  75                  80 gaa gag tct gta aaa gat act gga gac ctt gga gag agc ata gcc tta    288
Glu Glu Ser Val Lys Asp Thr Gly Asp Leu Gly Glu Ser Ile Ala Leu
                85                  90                  95 gct gta aag aaa aag aag cag aag agc ttc ttc tct cag ccc ctc aca    336
Ala Val Lys Lys Lys Lys Gln Lys Ser Phe Phe Ser Gln Pro Leu Thr
            100                 105                 110 ata aag agg gta tat caa acc ctt gta aag gtt gca gaa aca acg ggg    384
Ile Lys Arg Val Tyr Gln Thr Leu Val Lys Val Ala Glu Thr Thr Gly
        115                 120                 125 gag gga agc caa gat aaa aaa gta aag tat cta gct gat ttg ttc atg    432
Glu Gly Ser Gln Asp Lys Lys Val Lys Tyr Leu Ala Asp Leu Phe Met
    130                 135                 140 gac gca gaa cct tta gaa gct aag tat ctt gct cgt aca atc tta gga    480
Asp Ala Glu Pro Leu Glu Ala Lys Tyr Leu Ala Arg Thr Ile Leu Gly
145                 150                 155                 160 aca atg aga aca gga gtt gca gaa gga ttg ctt aga gat gca ata gca    528
Thr Met Arg Thr Gly Val Ala Glu Gly Leu Leu Arg Asp Ala Ile Ala
                165                 170                 175
```

```
atg gca ttc cac gta aag gta gag ctt gtt gag aga gct tac atg cta    576
Met Ala Phe His Val Lys Val Glu Leu Val Glu Arg Ala Tyr Met Leu
        180                 185                 190 acg agt gat ttc gga tat gta gct aaa ata gca aag ctt gaa gga aat    624
Thr Ser Asp Phe Gly Tyr Val Ala Lys Ile Ala Lys Leu Glu Gly Asn
    195                 200                 205 gaa ggg cta gca aaa gtt caa gtt caa ctc gga aag cca ata aag cca    672
Glu Gly Leu Ala Lys Val Gln Val Gln Leu Gly Lys Pro Ile Lys Pro
210                 215                 220 atg ctt gcc cag caa gct gct agc ata aga gat gca ctt ctc gag atg    720
Met Leu Ala Gln Gln Ala Ala Ser Ile Arg Asp Ala Leu Leu Glu Met
225                 230                 235                 240 ggt gga gag gca gag ttc gag att aaa tac gat gga gca agg gtg cag    768
Gly Gly Glu Ala Glu Phe Glu Ile Lys Tyr Asp Gly Ala Arg Val Gln
                245                 250                 255 gtg cac aag gat ggc tca aaa att ata gtc tat tct aga aga ctg gag    816
Val His Lys Asp Gly Ser Lys Ile Ile Val Tyr Ser Arg Arg Leu Glu
            260                 265                 270 aac gtc acc aga gcg att cca gaa att gtt gag gct cta aaa gag gca    864
Asn Val Thr Arg Ala Ile Pro Glu Ile Val Glu Ala Leu Lys Glu Ala
        275                 280                 285 ata ata cct gaa aag gca ata gtg gaa gga gaa ctt gtg gca att gga    912
Ile Ile Pro Glu Lys Ala Ile Val Glu Gly Glu Leu Val Ala Ile Gly
    290                 295                 300 gaa aac gga aga cca ttg ccc ttc caa tat gtg ctt aga agg ttt agg    960
Glu Asn Gly Arg Pro Leu Pro Phe Gln Tyr Val Leu Arg Arg Phe Arg
305                 310                 315                 320 aga aag cat aac ata gaa gaa atg atg gaa aag ata cct ctc gag ctc   1008
Arg Lys His Asn Ile Glu Glu Met Met Glu Lys Ile Pro Leu Glu Leu
                325                 330                 335 aac tta ttc gac gtt ctc tac gta gat gga caa agc ttg att gac act   1056
Asn Leu Phe Asp Val Leu Tyr Val Asp Gly Gln Ser Leu Ile Asp Thr
            340                 345                 350 aag ttc att gat aga aga aga aca ctt gaa gaa ata ata aag cag aat   1104
Lys Phe Ile Asp Arg Arg Arg Thr Leu Glu Glu Ile Ile Lys Gln Asn
        355                 360                 365 gaa aag ata aag gta gca gaa aac cta ata aca aag aaa gtc gag gaa   1152
Glu Lys Ile Lys Val Ala Glu Asn Leu Ile Thr Lys Lys Val Glu Glu
    370                 375                 380 gca gag gca ttt tac aag aga gca ctc gaa atg ggg cac gag gga ttg   1200
Ala Glu Ala Phe Tyr Lys Arg Ala Leu Glu Met Gly His Glu Gly Leu
385                 390                 395                 400 atg gcc aag agg tta gat gca gtc tac gaa cca ggt aac aga gga aag   1248
Met Ala Lys Arg Leu Asp Ala Val Tyr Glu Pro Gly Asn Arg Gly Lys
                405                 410                 415 aag tgg ttg aag ata aag ccc aca atg gag aac tta gat tta gta atc   1296
Lys Trp Leu Lys Ile Lys Pro Thr Met Glu Asn Leu Asp Leu Val Ile
            420                 425                 430 ata gga gca gaa tgg gga gag gga aga aga gcc cat ctc ttt ggt tca   1344
Ile Gly Ala Glu Trp Gly Glu Gly Arg Arg Ala His Leu Phe Gly Ser
        435                 440                 445 ttc atc ctg gga gca tat gat cca gaa aca gga gaa ttc cta gag gta   1392
Phe Ile Leu Gly Ala Tyr Asp Pro Glu Thr Gly Glu Phe Leu Glu Val
    450                 455                 460 gga aaa gtg gga agt gga ttc aca gat gat gac tta gtt gag ttt acg   1440
Gly Lys Val Gly Ser Gly Phe Thr Asp Asp Asp Leu Val Glu Phe Thr
465                 470                 475                 480 aag atg cta aag ccc ctt att ata aaa gag gaa gga aag aga gtc tgg   1488
Lys Met Leu Lys Pro Leu Ile Ile Lys Glu Glu Gly Lys Arg Val Trp
                485                 490                 495
```

```
ctc cag ccc aaa gtt gtt att gaa gtg aca tat caa gaa att cag aag    1536
Leu Gln Pro Lys Val Val Ile Glu Val Thr Tyr Gln Glu Ile Gln Lys
        500                 505                 510 agt cca aaa tac aga agt gga ttt gca tta agg ttc cca agg ttc gtt    1584
Ser Pro Lys Tyr Arg Ser Gly Phe Ala Leu Arg Phe Pro Arg Phe Val
        515                 520                 525 gca ctt aga gat gat aaa gga cca gaa gat gca gat aca ata gag aga    1632
Ala Leu Arg Asp Asp Lys Gly Pro Glu Asp Ala Asp Thr Ile Glu Arg
        530                 535                 540 atc gca caa ctt tac gag ttg caa gaa aag atg aaa gga aaa gtg gaa    1680
Ile Ala Gln Leu Tyr Glu Leu Gln Glu Lys Met Lys Gly Lys Val Glu
545                 550                 555                 560 agc                                                                 1683
Ser

<210> SEQ ID NO 2
<211> LENGTH: 561
<212> TYPE: PRT
<213> ORGANISM: Pyrococcus furiosus

<400> SEQUENCE: 2

Met Arg Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
            20                  25                  30

Val Pro Asp Asp His Leu Glu Phe Ile Pro Tyr Leu Ile Leu Gly Glu
        35                  40                  45

Val Phe Pro Glu Trp Asp Glu Arg Leu Gly Val Gly Glu Lys Leu
    50                  55                  60

Leu Ile Lys Ala Val Ala Met Ala Thr Gly Ile Asp Ala Lys Glu Ile
65                  70                  75                  80

Glu Glu Ser Val Lys Asp Thr Gly Asp Leu Gly Glu Ser Ile Ala Leu
                85                  90                  95

Ala Val Lys Lys Lys Gln Lys Ser Phe Phe Ser Gln Pro Leu Thr
            100                 105                 110

Ile Lys Arg Val Tyr Gln Thr Leu Val Lys Val Ala Glu Thr Thr Gly
        115                 120                 125

Glu Gly Ser Gln Asp Lys Lys Val Lys Tyr Leu Ala Asp Leu Phe Met
    130                 135                 140

Asp Ala Glu Pro Leu Glu Ala Lys Tyr Leu Ala Arg Thr Ile Leu Gly
145                 150                 155                 160

Thr Met Arg Thr Gly Val Ala Glu Gly Leu Leu Arg Asp Ala Ile Ala
                165                 170                 175

Met Ala Phe His Val Lys Val Glu Leu Val Arg Ala Tyr Met Leu
            180                 185                 190

Thr Ser Asp Phe Gly Tyr Val Ala Lys Ile Ala Lys Leu Glu Gly Asn
        195                 200                 205

Glu Gly Leu Ala Lys Val Gln Val Gln Leu Gly Lys Pro Ile Lys Pro
    210                 215                 220

Met Leu Ala Gln Gln Ala Ala Ser Ile Arg Asp Ala Leu Leu Glu Met
225                 230                 235                 240

Gly Gly Glu Ala Glu Phe Glu Ile Lys Tyr Asp Gly Ala Arg Val Gln
                245                 250                 255

Val His Lys Asp Gly Ser Lys Ile Ile Val Tyr Ser Arg Arg Leu Glu
            260                 265                 270

Asn Val Thr Arg Ala Ile Pro Glu Ile Val Glu Ala Leu Lys Glu Ala
```

```
                  275                 280                 285
Ile Ile Pro Glu Lys Ala Ile Val Glu Gly Glu Leu Val Ala Ile Gly
            290                 295                 300

Glu Asn Gly Arg Pro Leu Pro Phe Gln Tyr Val Leu Arg Arg Phe Arg
305                 310                 315                 320

Arg Lys His Asn Ile Glu Glu Met Met Glu Lys Ile Pro Leu Glu Leu
                325                 330                 335

Asn Leu Phe Asp Val Leu Tyr Val Asp Gly Gln Ser Leu Ile Asp Thr
            340                 345                 350

Lys Phe Ile Asp Arg Arg Thr Leu Glu Glu Ile Ile Lys Gln Asn
            355                 360                 365

Glu Lys Ile Lys Val Ala Glu Asn Leu Ile Thr Lys Lys Val Glu Glu
        370                 375                 380

Ala Glu Ala Phe Tyr Lys Arg Ala Leu Glu Met Gly His Glu Gly Leu
385                 390                 395                 400

Met Ala Lys Arg Leu Asp Ala Val Tyr Glu Pro Gly Asn Arg Gly Lys
            405                 410                 415

Lys Trp Leu Lys Ile Lys Pro Thr Met Glu Asn Leu Asp Leu Val Ile
            420                 425                 430

Ile Gly Ala Glu Trp Gly Glu Gly Arg Arg Ala His Leu Phe Gly Ser
        435                 440                 445

Phe Ile Leu Gly Ala Tyr Asp Pro Glu Thr Gly Glu Phe Leu Glu Val
        450                 455                 460

Gly Lys Val Gly Ser Gly Phe Thr Asp Asp Leu Val Glu Phe Thr
465                 470                 475                 480

Lys Met Leu Lys Pro Leu Ile Ile Lys Glu Glu Gly Lys Arg Val Trp
            485                 490                 495

Leu Gln Pro Lys Val Val Ile Glu Val Thr Tyr Gln Glu Ile Gln Lys
            500                 505                 510

Ser Pro Lys Tyr Arg Ser Gly Phe Ala Leu Arg Phe Pro Arg Phe Val
        515                 520                 525

Ala Leu Arg Asp Asp Lys Gly Pro Glu Asp Ala Asp Thr Ile Glu Arg
        530                 535                 540

Ile Ala Gln Leu Tyr Glu Leu Gln Glu Lys Met Lys Gly Lys Val Glu
545                 550                 555                 560

Ser

<210> SEQ ID NO 3
<211> LENGTH: 1683
<212> TYPE: DNA
<213> ORGANISM: Pyrococcus furiosus
<220> FEATURE:
<221> NAME/KEY: CDS
<222> LOCATION: (1)..(1683)

<400> SEQUENCE: 3 atg ggt tat cta gag ctt gct caa ctt tat caa aag tta gaa aag aca    48
Met Gly Tyr Leu Glu Leu Ala Gln Leu Tyr Gln Lys Leu Glu Lys Thr
1               5                  10                  15 act atg aaa ctt ata aag act aga ctt gtc gcc gac ttc ctg aaa aaa    96
Thr Met Lys Leu Ile Lys Thr Arg Leu Val Ala Asp Phe Leu Lys Lys
            20                  25                  30 gta cca gat gat cat ctg gag ttc att ccc tat cta att ctt gga gaa   144
Val Pro Asp Asp His Leu Glu Phe Ile Pro Tyr Leu Ile Leu Gly Glu
        35                  40                  45 gtt ttt cca gag tgg gat gaa agg gag ctg ggt gtg gga gaa aag ctg   192
Val Phe Pro Glu Trp Asp Glu Arg Glu Leu Gly Val Gly Glu Lys Leu
```

```
                50                      55                      60
tta att aaa gct gta gca atg gcc act gga att gac gca aaa gaa atc    240
Leu Ile Lys Ala Val Ala Met Ala Thr Gly Ile Asp Ala Lys Glu Ile
 65                  70                      75                  80 gaa gag tct gta aaa gat act gga gac ctt gga gag agc ata gcc tta    288
Glu Glu Ser Val Lys Asp Thr Gly Asp Leu Gly Glu Ser Ile Ala Leu
                 85                      90                      95 gct gta aag aaa aag aag cag aag agc ttc ttc tct cag ccc ctc aca    336
Ala Val Lys Lys Lys Lys Gln Lys Ser Phe Phe Ser Gln Pro Leu Thr
            100                     105                     110 ata aag agg gta tat caa acc ctt gta aag gtt gca gaa aca acg ggg    384
Ile Lys Arg Val Tyr Gln Thr Leu Val Lys Val Ala Glu Thr Thr Gly
                115                     120                     125 gag gga agc caa gat aaa aaa gta aag tat cta gct gat ttg ttc atg    432
Glu Gly Ser Gln Asp Lys Lys Val Lys Tyr Leu Ala Asp Leu Phe Met
        130                     135                     140 gac gca gaa cct tta gaa gct aag tat ctt gct cgt aca atc tta gga    480
Asp Ala Glu Pro Leu Glu Ala Lys Tyr Leu Ala Arg Thr Ile Leu Gly
145                     150                     155                 160 aca atg aga aca gga gtt gca gaa gga ttg ctt aga gat gca ata gca    528
Thr Met Arg Thr Gly Val Ala Glu Gly Leu Leu Arg Asp Ala Ile Ala
                    165                     170                     175 atg gca ttc cac gta aag gta gag ctt gtt gag aga gct tac atg cta    576
Met Ala Phe His Val Lys Val Glu Leu Val Glu Arg Ala Tyr Met Leu
                180                     185                     190 acg agt gat ttc gga tat gta gct aaa ata gca aag ctt gaa gga aat    624
Thr Ser Asp Phe Gly Tyr Val Ala Lys Ile Ala Lys Leu Glu Gly Asn
            195                     200                     205 gaa ggg cta gca aaa gtt caa gtt caa ctc gga aag cca ata aag cca    672
Glu Gly Leu Ala Lys Val Gln Val Gln Leu Gly Lys Pro Ile Lys Pro
        210                     215                     220 atg ctt gcc cag caa gct gct agc ata aga gat gca ctt ctc gag atg    720
Met Leu Ala Gln Gln Ala Ala Ser Ile Arg Asp Ala Leu Leu Glu Met
225                     230                     235                 240 ggt gga gag gca gag ttc gag att aaa tac gat gga gca agg gtg cag    768
Gly Gly Glu Ala Glu Phe Glu Ile Lys Tyr Asp Gly Ala Arg Val Gln
                    245                     250                     255 gtg cac aag gat ggc tca aaa att ata gtc tat tct aga aga ctg gag    816
Val His Lys Asp Gly Ser Lys Ile Ile Val Tyr Ser Arg Arg Leu Glu
                260                     265                     270 aac gtc acc aga gcg att cca gaa att gtt gag gct cta aaa gag gca    864
Asn Val Thr Arg Ala Ile Pro Glu Ile Val Glu Ala Leu Lys Glu Ala
            275                     280                     285 ata ata cct gaa aag gca ata gtg gaa gga gaa ctt gtg gca att gga    912
Ile Ile Pro Glu Lys Ala Ile Val Glu Gly Glu Leu Val Ala Ile Gly
        290                     295                     300 gaa aac gga aga cca ttg ccc ttc caa tat gtg ctt aga agg ttt agg    960
Glu Asn Gly Arg Pro Leu Pro Phe Gln Tyr Val Leu Arg Arg Phe Arg
305                     310                     315                 320 aga aag cat aac ata gaa gaa atg atg gaa aag ata cct ctc gag ctc   1008
Arg Lys His Asn Ile Glu Glu Met Met Glu Lys Ile Pro Leu Glu Leu
                    325                     330                     335 aac tta ttc gac gtt ctc tac gta gat gga caa agc ttg att gac act   1056
Asn Leu Phe Asp Val Leu Tyr Val Asp Gly Gln Ser Leu Ile Asp Thr
                340                     345                     350 aag ttc att gat aga aga aga aca ctt gaa gaa ata ata aag cag aat   1104
Lys Phe Ile Asp Arg Arg Arg Thr Leu Glu Glu Ile Ile Lys Gln Asn
            355                     360                     365 gaa aag ata aag gta gca gaa aac cta ata aca aag aaa gtc gag gaa   1152
Glu Lys Ile Lys Val Ala Glu Asn Leu Ile Thr Lys Lys Val Glu Glu
```

```
                                370                       375                       380
gca gag gca ttt tac aag aga gca ctc gaa atg ggg cac gag gga ttg     1200
Ala Glu Ala Phe Tyr Lys Arg Ala Leu Glu Met Gly His Glu Gly Leu
385                     390                     395                     400 atg gcc aag agg tta gat gca gtc tac gaa cca ggt aac aga gga aag     1248
Met Ala Lys Arg Leu Asp Ala Val Tyr Glu Pro Gly Asn Arg Gly Lys
                405                     410                     415 aag tgg ttg aag ata aag ccc aca atg gag aac tta gat tta gta atc     1296
Lys Trp Leu Lys Ile Lys Pro Thr Met Glu Asn Leu Asp Leu Val Ile
            420                     425                     430 ata gga gca gaa tgg gga gag gga aga aga gcc cat ctc ttt ggt tca     1344
Ile Gly Ala Glu Trp Gly Glu Gly Arg Arg Ala His Leu Phe Gly Ser
                    435                     440                     445 ttc atc ctg gga gca tat gat cca gaa aca gga gaa ttc cta gag gta     1392
Phe Ile Leu Gly Ala Tyr Asp Pro Glu Thr Gly Glu Phe Leu Glu Val
        450                     455                     460 gga aaa gtg gga agt gga ttc aca gat gat gac tta gtt gag ttt acg     1440
Gly Lys Val Gly Ser Gly Phe Thr Asp Asp Asp Leu Val Glu Phe Thr
465                     470                     475                     480 aag atg cta aag ccc ctt att ata aaa gag gaa gga aag aga gtc tgg     1488
Lys Met Leu Lys Pro Leu Ile Ile Lys Glu Glu Gly Lys Arg Val Trp
                485                     490                     495 ctc cag ccc aaa gtt gtt att gaa gtg aca tat caa gaa att cag aag     1536
Leu Gln Pro Lys Val Val Ile Glu Val Thr Tyr Gln Glu Ile Gln Lys
            500                     505                     510 agt cca aaa tac aga agt gga ttt gca tta agg ttc cca agg ttc gtt     1584
Ser Pro Lys Tyr Arg Ser Gly Phe Ala Leu Arg Phe Pro Arg Phe Val
                    515                     520                     525 gca ctt aga gat gat aaa gga cca gaa gat gca gat aca ata gag aga     1632
Ala Leu Arg Asp Asp Lys Gly Pro Glu Asp Ala Asp Thr Ile Glu Arg
        530                     535                     540 atc gca caa ctt tac gag ttg caa gaa aag atg aaa gga aaa gtg gaa     1680
Ile Ala Gln Leu Tyr Glu Leu Gln Glu Lys Met Lys Gly Lys Val Glu
545                     550                     555                     560 agc                                                                 1683
Ser

<210> SEQ ID NO 4
<211> LENGTH: 561
<212> TYPE: PRT
<213> ORGANISM: Pyrococcus furiosus

<400> SEQUENCE: 4

Met Gly Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
                20                  25                  30

Val Pro Asp Asp His Leu Glu Phe Ile Pro Tyr Leu Ile Leu Gly Glu
            35                  40                  45

Val Phe Pro Glu Trp Asp Glu Arg Leu Gly Val Gly Glu Lys Leu
        50                  55                  60

Leu Ile Lys Ala Val Ala Met Ala Thr Gly Ile Asp Ala Lys Glu Ile
65                  70                  75                  80

Glu Glu Ser Val Lys Asp Thr Gly Asp Leu Gly Glu Ser Ile Ala Leu
                85                  90                  95

Ala Val Lys Lys Lys Gln Lys Ser Phe Phe Ser Gln Pro Leu Thr
            100                 105                 110

Ile Lys Arg Val Tyr Gln Thr Leu Val Lys Val Ala Glu Thr Thr Gly
        115                 120                 125
```

-continued

Glu Gly Ser Gln Asp Lys Lys Val Lys Tyr Leu Ala Asp Leu Phe Met
            130                 135                 140

Asp Ala Glu Pro Leu Glu Ala Lys Tyr Leu Ala Arg Thr Ile Leu Gly
145                 150                 155                 160

Thr Met Arg Thr Gly Val Ala Glu Gly Leu Arg Asp Ala Ile Ala
                165                 170                 175

Met Ala Phe His Val Lys Val Glu Leu Val Glu Arg Ala Tyr Met Leu
            180                 185                 190

Thr Ser Asp Phe Gly Tyr Val Ala Lys Ile Ala Lys Leu Glu Gly Asn
            195                 200                 205

Glu Gly Leu Ala Lys Val Gln Val Gln Leu Gly Lys Pro Ile Lys Pro
            210                 215                 220

Met Leu Ala Gln Gln Ala Ala Ser Ile Arg Asp Ala Leu Leu Glu Met
225                 230                 235                 240

Gly Gly Glu Ala Glu Phe Glu Ile Lys Tyr Asp Gly Ala Arg Val Gln
                245                 250                 255

Val His Lys Asp Gly Ser Lys Ile Ile Val Tyr Ser Arg Arg Leu Glu
            260                 265                 270

Asn Val Thr Arg Ala Ile Pro Glu Ile Val Glu Ala Leu Lys Glu Ala
            275                 280                 285

Ile Ile Pro Glu Lys Ala Ile Val Glu Gly Glu Leu Val Ala Ile Gly
            290                 295                 300

Glu Asn Gly Arg Pro Leu Pro Phe Gln Tyr Val Leu Arg Arg Phe Arg
305                 310                 315                 320

Arg Lys His Asn Ile Glu Glu Met Met Glu Lys Ile Pro Leu Glu Leu
                325                 330                 335

Asn Leu Phe Asp Val Leu Tyr Val Asp Gly Gln Ser Leu Ile Asp Thr
            340                 345                 350

Lys Phe Ile Asp Arg Arg Thr Leu Glu Glu Ile Ile Lys Gln Asn
            355                 360                 365

Glu Lys Ile Lys Val Ala Glu Asn Leu Ile Thr Lys Lys Val Glu Glu
            370                 375                 380

Ala Glu Ala Phe Tyr Lys Arg Ala Leu Glu Met Gly His Glu Gly Leu
385                 390                 395                 400

Met Ala Lys Arg Leu Asp Ala Val Tyr Glu Pro Gly Asn Arg Gly Lys
                405                 410                 415

Lys Trp Leu Lys Ile Lys Pro Thr Met Glu Asn Leu Asp Leu Val Ile
                420                 425                 430

Ile Gly Ala Glu Trp Gly Glu Gly Arg Arg Ala His Leu Phe Gly Ser
            435                 440                 445

Phe Ile Leu Gly Ala Tyr Asp Pro Glu Thr Gly Glu Phe Leu Glu Val
            450                 455                 460

Gly Lys Val Gly Ser Gly Phe Thr Asp Asp Leu Val Glu Phe Thr
465                 470                 475                 480

Lys Met Leu Lys Pro Leu Ile Ile Lys Glu Glu Gly Lys Arg Val Trp
                485                 490                 495

Leu Gln Pro Lys Val Val Ile Glu Val Thr Tyr Gln Glu Ile Gln Lys
            500                 505                 510

Ser Pro Lys Tyr Arg Ser Gly Phe Ala Leu Arg Phe Pro Arg Phe Val
            515                 520                 525

Ala Leu Arg Asp Asp Lys Gly Pro Glu Asp Ala Asp Thr Ile Glu Arg
530                 535                 540

Ile Ala Gln Leu Tyr Glu Leu Gln Glu Lys Met Lys Gly Lys Val Glu

```
                      545               550                555                560
Ser

<210> SEQ ID NO 5
<211> LENGTH: 1683
<212> TYPE: DNA
<213> ORGANISM: Pyrococcus furiosus
<220> FEATURE:
<221> NAME/KEY: CDS
<222> LOCATION: (1)..(1683)

<400> SEQUENCE: 5 atg agg tat cta gag ctt gct caa ctt tat caa aag tta gaa aag aca      48
Met Arg Tyr Leu Glu Leu Ala Gln Leu Tyr Gln Lys Leu Glu Lys Thr
1               5                   10                  15 act atg aaa ctt ata aag act aga ctt gtc gcc gac ttc ctg aaa aaa      96
Thr Met Lys Leu Ile Lys Thr Arg Leu Val Ala Asp Phe Leu Lys Lys
            20                  25                  30 gta cca gat gat cat ctg gag ttc att ccc tat cta att ctt gga gaa     144
Val Pro Asp Asp His Leu Glu Phe Ile Pro Tyr Leu Ile Leu Gly Glu
        35                  40                  45 gtt ttt cca gag tgg gat gaa agg gag ctg ggt gtg gga gaa aag ctg     192
Val Phe Pro Glu Trp Asp Glu Arg Glu Leu Gly Val Gly Glu Lys Leu
    50                  55                  60 tta att aaa gct gta gca atg gcc act gga att gac gca aaa gaa atc     240
Leu Ile Lys Ala Val Ala Met Ala Thr Gly Ile Asp Ala Lys Glu Ile
65                  70                  75                  80 gaa gag tct gta aaa gat act gga gac ctt gga gag agc ata gcc tta     288
Glu Glu Ser Val Lys Asp Thr Gly Asp Leu Gly Glu Ser Ile Ala Leu
                85                  90                  95 gct gta aag aaa aag aag cag aag agc ttc ttc tct cag ccc ctc aca     336
Ala Val Lys Lys Lys Lys Gln Lys Ser Phe Phe Ser Gln Pro Leu Thr
            100                 105                 110 ata aag agg gta tat caa acc ctt gta aag gtt gca gaa aca acg ggg     384
Ile Lys Arg Val Tyr Gln Thr Leu Val Lys Val Ala Glu Thr Thr Gly
        115                 120                 125 gag gga agc caa gat aaa aaa gta aag tat cta gct gat ttg ttc atg     432
Glu Gly Ser Gln Asp Lys Lys Val Lys Tyr Leu Ala Asp Leu Phe Met
    130                 135                 140 gac gca gaa cct tta gaa gct aag tat ctt gct cgt aca atc tta gga     480
Asp Ala Glu Pro Leu Glu Ala Lys Tyr Leu Ala Arg Thr Ile Leu Gly
145                 150                 155                 160 aca atg aga aca gga gtt gca gaa gga ttg ctt aga gat gca ata gca     528
Thr Met Arg Thr Gly Val Ala Glu Gly Leu Leu Arg Asp Ala Ile Ala
                165                 170                 175 atg gca ttc cac gta aag gta gag ctt gtt gag aga gct tac atg cta     576
Met Ala Phe His Val Lys Val Glu Leu Val Glu Arg Ala Tyr Met Leu
            180                 185                 190 acg agt gat ttc gga tat gta gct aaa ata gca aag ctt gaa gga aat     624
Thr Ser Asp Phe Gly Tyr Val Ala Lys Ile Ala Lys Leu Glu Gly Asn
        195                 200                 205 gaa ggg cta gca aaa gtt caa gtt caa ctc gga aag cca ata aag cca     672
Glu Gly Leu Ala Lys Val Gln Val Gln Leu Gly Lys Pro Ile Lys Pro
    210                 215                 220 atg ctt gcc cag caa gct gct agc ata aga gat gca ctt ctc gag atg     720
Met Leu Ala Gln Gln Ala Ala Ser Ile Arg Asp Ala Leu Leu Glu Met
225                 230                 235                 240 ggt gga gag gca gag ttc gag att aaa tac gat gga gca agg gtg cag     768
Gly Gly Glu Ala Glu Phe Glu Ile Lys Tyr Asp Gly Ala Arg Val Gln
                245                 250                 255 gtg cac aag gat ggc tca aaa att ata gtc tat tct aga aga ctg gag     816
Val His Lys Asp Gly Ser Lys Ile Ile Val Tyr Ser Arg Arg Leu Glu
```

```
Val His Lys Asp Gly Ser Lys Ile Ile Val Tyr Ser Arg Arg Leu Glu
        260                 265                 270 aac gtc acc aga gcg att cca gaa att gtt gag gct cta aaa gag gca      864
Asn Val Thr Arg Ala Ile Pro Glu Ile Val Glu Ala Leu Lys Glu Ala
        275                 280                 285 ata ata cct gaa aag gca ata gtg gaa gga gaa ctt gtg gca att gga      912
Ile Ile Pro Glu Lys Ala Ile Val Glu Gly Glu Leu Val Ala Ile Gly
        290                 295                 300 gaa aac gga aga cca ttg ccc ttc caa tat gtg ctt aga agg ttt agg      960
Glu Asn Gly Arg Pro Leu Pro Phe Gln Tyr Val Leu Arg Arg Phe Arg
305                 310                 315                 320 aga aag cat aac ata gaa gaa atg atg gaa aag ata cct ctc gag ctc     1008
Arg Lys His Asn Ile Glu Glu Met Met Glu Lys Ile Pro Leu Glu Leu
                325                 330                 335 aac tta ttc gac gtt ctc tac gta gat gga caa agc ttg att gac act     1056
Asn Leu Phe Asp Val Leu Tyr Val Asp Gly Gln Ser Leu Ile Asp Thr
        340                 345                 350 aag ttc att gat aga aga aga aca ctt gaa gaa ata ata aag cag aat     1104
Lys Phe Ile Asp Arg Arg Arg Thr Leu Glu Glu Ile Ile Lys Gln Asn
        355                 360                 365 gaa aag ata aag gta gca gaa aac cta ata aca aag aaa gtc gag gaa     1152
Glu Lys Ile Lys Val Ala Glu Asn Leu Ile Thr Lys Lys Val Glu Glu
370                 375                 380 gca gag gca ttt tac aag aga gca ctc gaa atg ggg cac gag gga ttg     1200
Ala Glu Ala Phe Tyr Lys Arg Ala Leu Glu Met Gly His Glu Gly Leu
385                 390                 395                 400 atg gcc aag agg tta gat gca gtc tac gaa cca ggt aac aga gga aag     1248
Met Ala Lys Arg Leu Asp Ala Val Tyr Glu Pro Gly Asn Arg Gly Lys
        405                 410                 415 aag tgg ttg aag ata aag ccc aca atg gag aac tta gat tta gta atc     1296
Lys Trp Leu Lys Ile Lys Pro Thr Met Glu Asn Leu Asp Leu Val Ile
        420                 425                 430 ata gga gca gaa tgg gga gag gga aga aga gcc cat ctc ttt ggt tca     1344
Ile Gly Ala Glu Trp Gly Glu Gly Arg Arg Ala His Leu Phe Gly Ser
        435                 440                 445 ttc atc ctg gga gca tat gat cca gaa aca gga gaa ttc cta gag gta     1392
Phe Ile Leu Gly Ala Tyr Asp Pro Glu Thr Gly Glu Phe Leu Glu Val
450                 455                 460 gga aaa gtg gga agt gga ttc aca gat gat gac tta gtt gag ttt acg     1440
Gly Lys Val Gly Ser Gly Phe Thr Asp Asp Asp Leu Val Glu Phe Thr
465                 470                 475                 480 aag atg cta aag ccc ctt att ata aaa gag gaa gga aag aga gtc tgg     1488
Lys Met Leu Lys Pro Leu Ile Ile Lys Glu Glu Gly Lys Arg Val Trp
        485                 490                 495 ctc cag ccc aaa gtt gtt att gaa gtg aca tat caa gaa att cag aag     1536
Leu Gln Pro Lys Val Val Ile Glu Val Thr Tyr Gln Glu Ile Gln Lys
        500                 505                 510 agt cca aaa tac aga agt gga ttt gca tta agg ttc cca agg ttc gtt     1584
Ser Pro Lys Tyr Arg Ser Gly Phe Ala Leu Arg Phe Pro Arg Phe Val
        515                 520                 525 gca ctt aga gat gat aaa gga cca gaa gat gca gct aca ata gag aga     1632
Ala Leu Arg Asp Asp Lys Gly Pro Glu Asp Ala Ala Thr Ile Glu Arg
530                 535                 540 atc gca caa ctt tac gag ttg caa gaa aag atg aaa gga aaa gtg gaa     1680
Ile Ala Gln Leu Tyr Glu Leu Gln Glu Lys Met Lys Gly Lys Val Glu
545                 550                 555                 560 agc                                                                 1683
Ser
```

<210> SEQ ID NO 6

```
<211> LENGTH: 561
<212> TYPE: PRT
<213> ORGANISM: Pyrococcus furiosus

<400> SEQUENCE: 6
```

| | | | | | | | | | | | | | | |
|---|---|---|---|---|---|---|---|---|---|---|---|---|---|---|
| Met | Arg | Tyr | Leu | Glu | Leu | Ala | Gln | Leu | Tyr | Gln | Lys | Leu | Glu | Lys | Thr |
| 1 | | | | 5 | | | | | 10 | | | | | 15 | |
| Thr | Met | Lys | Leu | Ile | Lys | Thr | Arg | Leu | Val | Ala | Asp | Phe | Leu | Lys | Lys |
| | | | 20 | | | | | 25 | | | | | 30 | | |
| Val | Pro | Asp | Asp | His | Leu | Glu | Phe | Ile | Pro | Tyr | Leu | Ile | Leu | Gly | Glu |
| | | | | 35 | | | | | 40 | | | | 45 | | |
| Val | Phe | Pro | Glu | Trp | Asp | Glu | Arg | Glu | Leu | Gly | Val | Gly | Glu | Lys | Leu |
| | 50 | | | | | 55 | | | | | 60 | | | | |
| Leu | Ile | Lys | Ala | Val | Ala | Met | Ala | Thr | Gly | Ile | Asp | Ala | Lys | Glu | Ile |
| 65 | | | | | 70 | | | | | 75 | | | | | 80 |
| Glu | Glu | Ser | Val | Lys | Asp | Thr | Gly | Asp | Leu | Gly | Glu | Ser | Ile | Ala | Leu |
| | | | | 85 | | | | | 90 | | | | | 95 | |
| Ala | Val | Lys | Lys | Lys | Gln | Lys | Ser | Phe | Phe | Ser | Gln | Pro | Leu | Thr |
| | | | 100 | | | | | 105 | | | | | 110 | | |
| Ile | Lys | Arg | Val | Tyr | Gln | Thr | Leu | Val | Lys | Val | Ala | Glu | Thr | Thr | Gly |
| | | | 115 | | | | | 120 | | | | | 125 | | |
| Glu | Gly | Ser | Gln | Asp | Lys | Lys | Val | Lys | Tyr | Leu | Ala | Asp | Leu | Phe | Met |
| | 130 | | | | | 135 | | | | | 140 | | | | |
| Asp | Ala | Glu | Pro | Leu | Glu | Ala | Lys | Tyr | Leu | Ala | Arg | Thr | Ile | Leu | Gly |
| 145 | | | | | 150 | | | | | 155 | | | | | 160 |
| Thr | Met | Arg | Thr | Gly | Val | Ala | Glu | Gly | Leu | Leu | Arg | Asp | Ala | Ile | Ala |
| | | | | 165 | | | | | 170 | | | | | 175 | |
| Met | Ala | Phe | His | Val | Lys | Val | Glu | Leu | Val | Glu | Arg | Ala | Tyr | Met | Leu |
| | | | 180 | | | | | 185 | | | | | 190 | | |
| Thr | Ser | Asp | Phe | Gly | Tyr | Val | Ala | Lys | Ile | Ala | Lys | Leu | Glu | Gly | Asn |
| | | | 195 | | | | | 200 | | | | | 205 | | |
| Glu | Gly | Leu | Ala | Lys | Val | Gln | Val | Gln | Leu | Gly | Lys | Pro | Ile | Lys | Pro |
| | 210 | | | | | 215 | | | | | 220 | | | | |
| Met | Leu | Ala | Gln | Gln | Ala | Ala | Ser | Ile | Arg | Asp | Ala | Leu | Leu | Glu | Met |
| 225 | | | | | 230 | | | | | 235 | | | | | 240 |
| Gly | Gly | Glu | Ala | Glu | Phe | Glu | Ile | Lys | Tyr | Asp | Gly | Ala | Arg | Val | Gln |
| | | | | 245 | | | | | 250 | | | | | 255 | |
| Val | His | Lys | Asp | Gly | Ser | Lys | Ile | Ile | Val | Tyr | Ser | Arg | Arg | Leu | Glu |
| | | | 260 | | | | | 265 | | | | | 270 | | |
| Asn | Val | Thr | Arg | Ala | Ile | Pro | Glu | Ile | Val | Glu | Ala | Leu | Lys | Glu | Ala |
| | | | 275 | | | | | 280 | | | | | 285 | | |
| Ile | Ile | Pro | Glu | Lys | Ala | Ile | Val | Glu | Gly | Glu | Leu | Val | Ala | Ile | Gly |
| | 290 | | | | | 295 | | | | | 300 | | | | |
| Glu | Asn | Gly | Arg | Pro | Leu | Pro | Phe | Gln | Tyr | Val | Leu | Arg | Arg | Phe | Arg |
| 305 | | | | | 310 | | | | | 315 | | | | | 320 |
| Arg | Lys | His | Asn | Ile | Glu | Glu | Met | Met | Glu | Lys | Ile | Pro | Leu | Glu | Leu |
| | | | | 325 | | | | | 330 | | | | | 335 | |
| Asn | Leu | Phe | Asp | Val | Leu | Tyr | Val | Asp | Gly | Gln | Ser | Leu | Ile | Asp | Thr |
| | | | 340 | | | | | 345 | | | | | 350 | | |
| Lys | Phe | Ile | Asp | Arg | Arg | Arg | Thr | Leu | Glu | Glu | Ile | Ile | Lys | Gln | Asn |
| | | | 355 | | | | | 360 | | | | | 365 | | |
| Glu | Lys | Ile | Lys | Val | Ala | Glu | Asn | Leu | Ile | Thr | Lys | Lys | Val | Glu | Glu |
| | 370 | | | | | 375 | | | | | 380 | | | | |
| Ala | Glu | Ala | Phe | Tyr | Lys | Arg | Ala | Leu | Glu | Met | Gly | His | Glu | Gly | Leu |
| 385 | | | | | 390 | | | | | 395 | | | | | 400 |

```
Met Ala Lys Arg Leu Asp Ala Val Tyr Glu Pro Gly Asn Arg Gly Lys
                405                 410                 415

Lys Trp Leu Lys Ile Lys Pro Thr Met Glu Asn Leu Asp Leu Val Ile
            420                 425                 430

Ile Gly Ala Glu Trp Gly Glu Gly Arg Arg Ala His Leu Phe Gly Ser
        435                 440                 445

Phe Ile Leu Gly Ala Tyr Asp Pro Glu Thr Gly Glu Phe Leu Glu Val
    450                 455                 460

Gly Lys Val Gly Ser Gly Phe Thr Asp Asp Leu Val Glu Phe Thr
465                 470                 475                 480

Lys Met Leu Lys Pro Leu Ile Ile Lys Glu Glu Gly Lys Arg Val Trp
                485                 490                 495

Leu Gln Pro Lys Val Val Ile Glu Val Thr Tyr Gln Glu Ile Gln Lys
            500                 505                 510

Ser Pro Lys Tyr Arg Ser Gly Phe Ala Leu Arg Phe Pro Arg Phe Val
        515                 520                 525

Ala Leu Arg Asp Asp Lys Gly Pro Glu Asp Ala Ala Thr Ile Glu Arg
    530                 535                 540

Ile Ala Gln Leu Tyr Glu Leu Gln Glu Lys Met Lys Gly Lys Val Glu
545                 550                 555                 560

Ser

<210> SEQ ID NO 7
<211> LENGTH: 1683
<212> TYPE: DNA
<213> ORGANISM: Pyrococcus furiosus
<220> FEATURE:
<221> NAME/KEY: CDS
<222> LOCATION: (1)..(1683)

<400> SEQUENCE: 7 atg agg tat cta gag ctt gct caa ctt tat caa aag tta gaa aag aca      48
Met Arg Tyr Leu Glu Leu Ala Gln Leu Tyr Gln Lys Leu Glu Lys Thr
1               5                   10                  15 act atg aaa ctt ata aag act aga ctt gtc gcc gac ttc ctg aaa aaa      96
Thr Met Lys Leu Ile Lys Thr Arg Leu Val Ala Asp Phe Leu Lys Lys
            20                  25                  30 gta cca gat gat cat ctg gag ttc att ccc tat cta att ctt gga gaa     144
Val Pro Asp Asp His Leu Glu Phe Ile Pro Tyr Leu Ile Leu Gly Glu
        35                  40                  45 gtt ttt cca gag tgg gat gaa agg gag ctg ggt gtg gga gaa aag ctg     192
Val Phe Pro Glu Trp Asp Glu Arg Glu Leu Gly Val Gly Glu Lys Leu
    50                  55                  60 tta att aaa gct gta gca atg gcc act gga att gac gca aaa gaa atc     240
Leu Ile Lys Ala Val Ala Met Ala Thr Gly Ile Asp Ala Lys Glu Ile
65                  70                  75                  80 gaa gag tct gta aaa gat act gga gac ctt gga gag agc ata gcc tta     288
Glu Glu Ser Val Lys Asp Thr Gly Asp Leu Gly Glu Ser Ile Ala Leu
                85                  90                  95 gct gta aag aaa aag aag cag aag agc ttc ttc tct cag ccc ctc aca     336
Ala Val Lys Lys Lys Lys Gln Lys Ser Phe Phe Ser Gln Pro Leu Thr
            100                 105                 110 ata aag agg gta tat caa acc ctt gta aag gtt gca gaa aca acg ggg     384
Ile Lys Arg Val Tyr Gln Thr Leu Val Lys Val Ala Glu Thr Thr Gly
        115                 120                 125 gag gga agc caa gat aaa aaa gta aag tat cta gct gat ttg ttc atg     432
Glu Gly Ser Gln Asp Lys Lys Val Lys Tyr Leu Ala Asp Leu Phe Met
    130                 135                 140
```

-continued

| | |
|---|---|
| gac gca gaa cct tta gaa gct aag tat ctt gct cgt aca atc tta gga<br>Asp Ala Glu Pro Leu Glu Ala Lys Tyr Leu Ala Arg Thr Ile Leu Gly<br>145                      150                      155                      160 | 480 |
| aca atg aga aca gga gtt gca gaa gga ttg ctt aga gat gca ata gca<br>Thr Met Arg Thr Gly Val Ala Glu Gly Leu Leu Arg Asp Ala Ile Ala<br>                      165                      170                      175 | 528 |
| atg gca ttc cac gta aag gta gag ctt gtt gag aga gct tac atg cta<br>Met Ala Phe His Val Lys Val Glu Leu Val Glu Arg Ala Tyr Met Leu<br>                180                      185                      190 | 576 |
| acg agt gat ttc gga tat gta gct aaa ata gca aag ctt gaa gga aat<br>Thr Ser Asp Phe Gly Tyr Val Ala Lys Ile Ala Lys Leu Glu Gly Asn<br>              195                      200                      205 | 624 |
| gaa ggg cta gca aaa gtt caa gtt caa ctc gga aag cca ata aag cca<br>Glu Gly Leu Ala Lys Val Gln Val Gln Leu Gly Lys Pro Ile Lys Pro<br>210                      215                      220 | 672 |
| atg ctt gcc cag caa gct gct agc ata aga gat gca ctt ctc gag atg<br>Met Leu Ala Gln Gln Ala Ala Ser Ile Arg Asp Ala Leu Leu Glu Met<br>225                      230                      235                      240 | 720 |
| ggt gga gag gca gag ttc gag att aaa tac gat gga gca agg gtg cag<br>Gly Gly Glu Ala Glu Phe Glu Ile Lys Tyr Asp Gly Ala Arg Val Gln<br>                      245                      250                      255 | 768 |
| gtg cac aag gat ggc tca aaa att ata gtc tat tct aga aga ctg gag<br>Val His Lys Asp Gly Ser Lys Ile Ile Val Tyr Ser Arg Arg Leu Glu<br>            260                      265                      270 | 816 |
| aac gtc acc aga gcg att cca gaa att gtt gag gct cta aaa gag gca<br>Asn Val Thr Arg Ala Ile Pro Glu Ile Val Glu Ala Leu Lys Glu Ala<br>            275                      280                      285 | 864 |
| ata ata cct gaa aag gca ata gtg gaa gga gaa ctt gtg gca att gga<br>Ile Ile Pro Glu Lys Ala Ile Val Glu Gly Glu Leu Val Ala Ile Gly<br>        290                      295                      300 | 912 |
| gaa aac gga aga cca ttg ccc ttc caa tat gtg ctt aga agg ttt agg<br>Glu Asn Gly Arg Pro Leu Pro Phe Gln Tyr Val Leu Arg Arg Phe Arg<br>305                      310                      315                      320 | 960 |
| aga aag cat aac ata gaa gaa atg atg gaa aag ata cct ctc gag ctc<br>Arg Lys His Asn Ile Glu Glu Met Met Glu Lys Ile Pro Leu Glu Leu<br>                      325                      330                      335 | 1008 |
| aac tta ttc gac gtt ctc tac gta gat gga caa agc ttg att gac act<br>Asn Leu Phe Asp Val Leu Tyr Val Asp Gly Gln Ser Leu Ile Asp Thr<br>            340                      345                      350 | 1056 |
| aag ttc att gat aga aga aga aca ctt gaa gaa ata ata aag cag aat<br>Lys Phe Ile Asp Arg Arg Arg Thr Leu Glu Glu Ile Ile Lys Gln Asn<br>              355                      360                      365 | 1104 |
| gaa aag ata aag gta gca gaa aac cta ata aca aag aaa gtc gag gaa<br>Glu Lys Ile Lys Val Ala Glu Asn Leu Ile Thr Lys Lys Val Glu Glu<br>370                      375                      380 | 1152 |
| gca gag gca ttt tac aag aga gca ctc gaa atg ggg cac gag gga ttg<br>Ala Glu Ala Phe Tyr Lys Arg Ala Leu Glu Met Gly His Glu Gly Leu<br>385                      390                      395                      400 | 1200 |
| atg gcc aag agg tta gat gca gtc tac gaa cca ggt aac aga gga aag<br>Met Ala Lys Arg Leu Asp Ala Val Tyr Glu Pro Gly Asn Arg Gly Lys<br>                      405                      410                      415 | 1248 |
| aag tgg ttg aag ata aag ccc aca atg gag aac tta gat tta gta atc<br>Lys Trp Leu Lys Ile Lys Pro Thr Met Glu Asn Leu Asp Leu Val Ile<br>              420                      425                      430 | 1296 |
| ata gga gca gaa tgg gga gag gga aga aga gcc cat ctc ttt ggt tca<br>Ile Gly Ala Glu Trp Gly Glu Gly Arg Arg Ala His Leu Phe Gly Ser<br>            435                      440                      445 | 1344 |
| ttc atc ctg gga gca tat gat cca gaa aca gga gaa ttc cta gag gta<br>Phe Ile Leu Gly Ala Tyr Asp Pro Glu Thr Gly Glu Phe Leu Glu Val<br>450                      455                      460 | 1392 |

-continued

```
gga aaa gtg gga agt gga ttc aca gat gat gac tta gtt gag ttt acg    1440
Gly Lys Val Gly Ser Gly Phe Thr Asp Asp Asp Leu Val Glu Phe Thr
465             470                 475                 480 aag atg cta aag ccc ctt att ata aaa gag gaa gga aag aga gtc tgg    1488
Lys Met Leu Lys Pro Leu Ile Ile Lys Glu Glu Gly Lys Arg Val Trp
                485                 490                 495 ctc cag ccc aaa gtt gtt att gaa gtg aca tat caa gaa att cag aag    1536
Leu Gln Pro Lys Val Val Ile Glu Val Thr Tyr Gln Glu Ile Gln Lys
            500                 505                 510 agt cca aaa tac aga agt gga ttt gca tta agg ttc cca agg ttc gtt    1584
Ser Pro Lys Tyr Arg Ser Gly Phe Ala Leu Arg Phe Pro Arg Phe Val
        515                 520                 525 gca ctt aga gat gat aaa gga cca gaa gat gca tct aca ata gag aga    1632
Ala Leu Arg Asp Asp Lys Gly Pro Glu Asp Ala Ser Thr Ile Glu Arg
    530                 535                 540 atc gca caa ctt tac gag ttg caa gaa aag atg aaa gga aaa gtg gaa    1680
Ile Ala Gln Leu Tyr Glu Leu Gln Glu Lys Met Lys Gly Lys Val Glu
545                 550                 555                 560 agc                                                                1683
Ser
```

<210> SEQ ID NO 8
<211> LENGTH: 561
<212> TYPE: PRT
<213> ORGANISM: Pyrococcus furiosus

<400> SEQUENCE: 8

Met Arg Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
                20                  25                  30

Val Pro Asp Asp His Leu Glu Phe Ile Pro Tyr Leu Ile Leu Gly Glu
            35                  40                  45

Val Phe Pro Glu Trp Asp Glu Arg Glu Leu Gly Val Gly Glu Lys Leu
        50                  55                  60

Leu Ile Lys Ala Val Ala Met Ala Thr Gly Ile Asp Ala Lys Glu Ile
65                  70                  75                  80

Glu Glu Ser Val Lys Asp Thr Gly Asp Leu Gly Glu Ser Ile Ala Leu
                85                  90                  95

Ala Val Lys Lys Lys Gln Lys Ser Phe Phe Ser Gln Pro Leu Thr
                100                 105                 110

Ile Lys Arg Val Tyr Gln Thr Leu Val Lys Val Ala Glu Thr Thr Gly
            115                 120                 125

Glu Gly Ser Gln Asp Lys Lys Val Lys Tyr Leu Ala Asp Leu Phe Met
        130                 135                 140

Asp Ala Glu Pro Leu Glu Ala Lys Tyr Leu Ala Arg Thr Ile Leu Gly
145                 150                 155                 160

Thr Met Arg Thr Gly Val Ala Glu Gly Leu Leu Arg Asp Ala Ile Ala
                165                 170                 175

Met Ala Phe His Val Lys Val Glu Leu Val Glu Arg Ala Tyr Met Leu
            180                 185                 190

Thr Ser Asp Phe Gly Tyr Val Ala Lys Ile Ala Lys Leu Glu Gly Asn
        195                 200                 205

Glu Gly Leu Ala Lys Val Gln Val Gln Leu Gly Lys Pro Ile Lys Pro
    210                 215                 220

Met Leu Ala Gln Gln Ala Ala Ser Ile Arg Asp Ala Leu Leu Glu Met
225                 230                 235                 240

```
Gly Gly Glu Ala Glu Phe Glu Ile Lys Tyr Asp Gly Ala Arg Val Gln
                245                 250                 255

Val His Lys Asp Gly Ser Lys Ile Ile Val Tyr Ser Arg Arg Leu Glu
            260                 265                 270

Asn Val Thr Arg Ala Ile Pro Glu Ile Val Glu Ala Leu Lys Glu Ala
        275                 280                 285

Ile Ile Pro Glu Lys Ala Ile Val Glu Gly Leu Val Ala Ile Gly
    290                 295                 300

Glu Asn Gly Arg Pro Leu Pro Phe Gln Tyr Val Leu Arg Arg Phe Arg
305                 310                 315                 320

Arg Lys His Asn Ile Glu Glu Met Met Glu Lys Ile Pro Leu Glu Leu
                325                 330                 335

Asn Leu Phe Asp Val Leu Tyr Val Asp Gly Gln Ser Leu Ile Asp Thr
            340                 345                 350

Lys Phe Ile Asp Arg Arg Arg Thr Leu Glu Glu Ile Ile Lys Gln Asn
        355                 360                 365

Glu Lys Ile Lys Val Ala Glu Asn Leu Ile Thr Lys Lys Val Glu Glu
    370                 375                 380

Ala Glu Ala Phe Tyr Lys Arg Ala Leu Glu Met Gly His Glu Gly Leu
385                 390                 395                 400

Met Ala Lys Arg Leu Asp Ala Val Tyr Glu Pro Gly Asn Arg Gly Lys
                405                 410                 415

Lys Trp Leu Lys Ile Lys Pro Thr Met Glu Asn Leu Asp Leu Val Ile
            420                 425                 430

Ile Gly Ala Glu Trp Gly Glu Gly Arg Arg Ala His Leu Phe Gly Ser
        435                 440                 445

Phe Ile Leu Gly Ala Tyr Asp Pro Glu Thr Gly Glu Phe Leu Glu Val
    450                 455                 460

Gly Lys Val Gly Ser Gly Phe Thr Asp Asp Leu Val Glu Phe Thr
465                 470                 475                 480

Lys Met Leu Lys Pro Leu Ile Ile Lys Glu Glu Gly Lys Arg Val Trp
                485                 490                 495

Leu Gln Pro Lys Val Val Ile Glu Val Thr Tyr Gln Glu Ile Gln Lys
            500                 505                 510

Ser Pro Lys Tyr Arg Ser Gly Phe Ala Leu Arg Phe Pro Arg Phe Val
        515                 520                 525

Ala Leu Arg Asp Asp Lys Gly Pro Glu Asp Ala Ser Thr Ile Glu Arg
    530                 535                 540

Ile Ala Gln Leu Tyr Glu Leu Gln Glu Lys Met Lys Gly Lys Val Glu
545                 550                 555                 560

Ser

<210> SEQ ID NO 9
<211> LENGTH: 1683
<212> TYPE: DNA
<213> ORGANISM: Pyrococcus furiosus
<220> FEATURE:
<221> NAME/KEY: CDS
<222> LOCATION: (1)..(1683)

<400> SEQUENCE: 9 atg agg tat cta gag ctt gct caa ctt tat caa aag tta gaa aag aca      48
Met Arg Tyr Leu Glu Leu Ala Gln Leu Tyr Gln Lys Leu Glu Lys Thr
1               5                   10                  15 act atg aaa ctt ata aag act aga ctt gtc gcc gac ttc ctg aaa aaa      96
Thr Met Lys Leu Ile Lys Thr Arg Leu Val Ala Asp Phe Leu Lys Lys
            20                  25                  30
```

```
gta cca gat gat cat ctg gag ttc att ccc tat cta att ctt gga gaa      144
Val Pro Asp Asp His Leu Glu Phe Ile Pro Tyr Leu Ile Leu Gly Glu
        35                  40                  45 gtt ttt cca gag tgg gat gaa agg gag ctg ggt gtg gga gaa aag ctg      192
Val Phe Pro Glu Trp Asp Glu Arg Glu Leu Gly Val Gly Glu Lys Leu
 50                  55                  60 tta att aaa gct gta gca atg gcc act gga att gac gca aaa gaa atc      240
Leu Ile Lys Ala Val Ala Met Ala Thr Gly Ile Asp Ala Lys Glu Ile
 65                  70                  75                  80 gaa gag tct gta aaa gat act gga gac ctt gga gag agc ata gcc tta      288
Glu Glu Ser Val Lys Asp Thr Gly Asp Leu Gly Glu Ser Ile Ala Leu
                 85                  90                  95 gct gta aag aaa aag aag cag aag agc ttc ttc tct cag ccc ctc aca      336
Ala Val Lys Lys Lys Lys Gln Lys Ser Phe Phe Ser Gln Pro Leu Thr
            100                 105                 110 ata aag agg gta tat caa acc ctt gta aag gtt gca gaa aca acg ggg      384
Ile Lys Arg Val Tyr Gln Thr Leu Val Lys Val Ala Glu Thr Thr Gly
        115                 120                 125 gag gga agc caa gat aaa aaa gta aag tat cta gct gat ttg ttc atg      432
Glu Gly Ser Gln Asp Lys Lys Val Lys Tyr Leu Ala Asp Leu Phe Met
130                 135                 140 gac gca gaa cct tta gaa gct aag tat ctt gct cgt aca atc tta gga      480
Asp Ala Glu Pro Leu Glu Ala Lys Tyr Leu Ala Arg Thr Ile Leu Gly
145                 150                 155                 160 aca atg aga aca gga gtt gca gaa gga ttg ctt aga gat gca ata gca      528
Thr Met Arg Thr Gly Val Ala Glu Gly Leu Leu Arg Asp Ala Ile Ala
                165                 170                 175 atg gca ttc cac gta aag gta gag ctt gtt gag aga gct tac atg cta      576
Met Ala Phe His Val Lys Val Glu Leu Val Glu Arg Ala Tyr Met Leu
            180                 185                 190 acg agt gat ttc gga tat gta gct aaa ata gca aag ctt gaa gga aat      624
Thr Ser Asp Phe Gly Tyr Val Ala Lys Ile Ala Lys Leu Glu Gly Asn
        195                 200                 205 gaa ggg cta gca aaa gtt caa gtt caa ctc gga aag cca ata aag cca      672
Glu Gly Leu Ala Lys Val Gln Val Gln Leu Gly Lys Pro Ile Lys Pro
210                 215                 220 atg ctt gcc cag caa gct gct agc ata aga gat gca ctt ctc gag atg      720
Met Leu Ala Gln Gln Ala Ala Ser Ile Arg Asp Ala Leu Leu Glu Met
225                 230                 235                 240 ggt gga gag gca gag ttc gag att aaa tac gat gga gca agg gtg cag      768
Gly Gly Glu Ala Glu Phe Glu Ile Lys Tyr Asp Gly Ala Arg Val Gln
                245                 250                 255 gtg cac aag gat ggc tca aaa att ata gtc tat tct aga aga ctg gag      816
Val His Lys Asp Gly Ser Lys Ile Ile Val Tyr Ser Arg Arg Leu Glu
            260                 265                 270 aac gtc acc aga gcg att cca gaa att gtt gag gct cta aaa gag gca      864
Asn Val Thr Arg Ala Ile Pro Glu Ile Val Glu Ala Leu Lys Glu Ala
        275                 280                 285 ata ata cct gaa aag gca ata gtg gaa gga gaa ctt gtg gca att gga      912
Ile Ile Pro Glu Lys Ala Ile Val Glu Gly Glu Leu Val Ala Ile Gly
    290                 295                 300 gaa aac gga aga cca ttg ccc ttc caa tat gtg ctt aga agg ttt agg      960
Glu Asn Gly Arg Pro Leu Pro Phe Gln Tyr Val Leu Arg Arg Phe Arg
305                 310                 315                 320 aga aag cat aac ata gaa gaa atg atg gaa aag ata cct ctc gag ctc     1008
Arg Lys His Asn Ile Glu Glu Met Met Glu Lys Ile Pro Leu Glu Leu
                325                 330                 335 aac tta ttc gac gtt ctc tac gta gat gga caa agc ttg att gac act     1056
Asn Leu Phe Asp Val Leu Tyr Val Asp Gly Gln Ser Leu Ile Asp Thr
            340                 345                 350
```

```
aag ttc att gat aga aga aga aca ctt gaa gaa ata ata aag cag aat      1104
Lys Phe Ile Asp Arg Arg Arg Thr Leu Glu Glu Ile Ile Lys Gln Asn
        355                 360                 365 gaa aag ata aag gta gca gaa aac cta ata aca aag aaa gtc gag gaa      1152
Glu Lys Ile Lys Val Ala Glu Asn Leu Ile Thr Lys Lys Val Glu Glu
370                 375                 380 gca gag gca ttt tac aag aga gca ctc gaa atg ggg cac gag gga ttg      1200
Ala Glu Ala Phe Tyr Lys Arg Ala Leu Glu Met Gly His Glu Gly Leu
385                 390                 395                 400 atg gcc aag agg tta gat gca gtc tac gaa cca ggt aac aga gga aag      1248
Met Ala Lys Arg Leu Asp Ala Val Tyr Glu Pro Gly Asn Arg Gly Lys
                405                 410                 415 aag tgg ttg aag ata aag ccc aca atg gag aac tta gat tta gta atc      1296
Lys Trp Leu Lys Ile Lys Pro Thr Met Glu Asn Leu Asp Leu Val Ile
        420                 425                 430 ata gga gca gaa tgg gga gag gga aga aga gcc cat ctc ttt ggt tca      1344
Ile Gly Ala Glu Trp Gly Glu Gly Arg Arg Ala His Leu Phe Gly Ser
435                 440                 445 ttc atc ctg gga gca tat gat cca gaa aca gga gaa ttc cta gag gta      1392
Phe Ile Leu Gly Ala Tyr Asp Pro Glu Thr Gly Glu Phe Leu Glu Val
450                 455                 460 gga aaa gtg gga agt gga ttc aca gat gat gac tta gtt gag ttt acg      1440
Gly Lys Val Gly Ser Gly Phe Thr Asp Asp Asp Leu Val Glu Phe Thr
465                 470                 475                 480 aag atg cta aag ccc ctt att ata aag gag gaa gga aag aga gtc tgg      1488
Lys Met Leu Lys Pro Leu Ile Ile Lys Glu Glu Gly Lys Arg Val Trp
                485                 490                 495 ctc cag ccc aaa gtt gtt att gaa gtg aca tat caa gaa att cag aag      1536
Leu Gln Pro Lys Val Val Ile Glu Val Thr Tyr Gln Glu Ile Gln Lys
        500                 505                 510 agt cca aaa tac aga agt gga ttt gca tta agg ttc cca agg ttc gtt      1584
Ser Pro Lys Tyr Arg Ser Gly Phe Ala Leu Arg Phe Pro Arg Phe Val
515                 520                 525 gca ctt aga gat gat aaa gga cca gaa gat gca cgt aca ata gag aga      1632
Ala Leu Arg Asp Asp Lys Gly Pro Glu Asp Ala Arg Thr Ile Glu Arg
530                 535                 540 atc gca caa ctt tac gag ttg caa gaa aag atg aaa gga aaa gtg gaa      1680
Ile Ala Gln Leu Tyr Glu Leu Gln Glu Lys Met Lys Gly Lys Val Glu
545                 550                 555                 560 agc                                                                  1683
Ser

<210> SEQ ID NO 10
<211> LENGTH: 561
<212> TYPE: PRT
<213> ORGANISM: Pyrococcus furiosus

<400> SEQUENCE: 10

Met Arg Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
            20                  25                  30

Val Pro Asp Asp His Leu Glu Phe Ile Pro Tyr Leu Ile Leu Gly Glu
        35                  40                  45

Val Phe Pro Glu Trp Asp Glu Arg Glu Leu Gly Val Gly Glu Lys Leu
    50                  55                  60

Leu Ile Lys Ala Val Ala Met Ala Thr Gly Ile Asp Ala Lys Glu Ile
65                  70                  75                  80

Glu Glu Ser Val Lys Asp Thr Gly Asp Leu Gly Glu Ser Ile Ala Leu
```

```
                85                  90                  95
Ala Val Lys Lys Lys Gln Lys Ser Phe Phe Ser Gln Pro Leu Thr
            100                 105                 110
Ile Lys Arg Val Tyr Gln Thr Leu Val Lys Val Ala Glu Thr Thr Gly
            115                 120                 125
Glu Gly Ser Gln Asp Lys Lys Val Lys Tyr Leu Ala Asp Leu Phe Met
            130                 135                 140
Asp Ala Glu Pro Leu Glu Ala Lys Tyr Leu Ala Arg Thr Ile Leu Gly
145                 150                 155                 160
Thr Met Arg Thr Gly Val Ala Glu Gly Leu Leu Arg Asp Ala Ile Ala
                165                 170                 175
Met Ala Phe His Val Lys Val Glu Leu Val Glu Arg Ala Tyr Met Leu
                180                 185                 190
Thr Ser Asp Phe Gly Tyr Val Ala Lys Ile Ala Lys Leu Glu Gly Asn
                195                 200                 205
Glu Gly Leu Ala Lys Val Gln Val Gln Leu Gly Lys Pro Ile Lys Pro
            210                 215                 220
Met Leu Ala Gln Gln Ala Ala Ser Ile Arg Asp Ala Leu Leu Glu Met
225                 230                 235                 240
Gly Gly Glu Ala Glu Phe Glu Ile Lys Tyr Asp Gly Ala Arg Val Gln
                245                 250                 255
Val His Lys Asp Gly Ser Lys Ile Ile Val Tyr Ser Arg Arg Leu Glu
            260                 265                 270
Asn Val Thr Arg Ala Ile Pro Glu Ile Val Glu Ala Leu Lys Glu Ala
            275                 280                 285
Ile Ile Pro Glu Lys Ala Ile Val Glu Gly Glu Leu Val Ala Ile Gly
            290                 295                 300
Glu Asn Gly Arg Pro Leu Pro Phe Gln Tyr Val Leu Arg Arg Phe Arg
305                 310                 315                 320
Arg Lys His Asn Ile Glu Glu Met Met Glu Lys Ile Pro Leu Glu Leu
                325                 330                 335
Asn Leu Phe Asp Val Leu Tyr Val Asp Gly Gln Ser Leu Ile Asp Thr
                340                 345                 350
Lys Phe Ile Asp Arg Arg Thr Leu Glu Glu Ile Ile Lys Gln Asn
            355                 360                 365
Glu Lys Ile Lys Val Ala Glu Asn Leu Ile Thr Lys Lys Val Glu Glu
            370                 375                 380
Ala Glu Ala Phe Tyr Lys Arg Ala Leu Glu Met Gly His Glu Gly Leu
385                 390                 395                 400
Met Ala Lys Arg Leu Asp Ala Val Tyr Glu Pro Gly Asn Arg Gly Lys
                405                 410                 415
Lys Trp Leu Lys Ile Lys Pro Thr Met Glu Asn Leu Asp Leu Val Ile
                420                 425                 430
Ile Gly Ala Glu Trp Gly Glu Gly Arg Arg Ala His Leu Phe Gly Ser
                435                 440                 445
Phe Ile Leu Gly Ala Tyr Asp Pro Glu Thr Gly Glu Phe Leu Glu Val
            450                 455                 460
Gly Lys Val Gly Ser Gly Phe Thr Asp Asp Leu Val Glu Phe Thr
465                 470                 475                 480
Lys Met Leu Lys Pro Leu Ile Ile Lys Glu Glu Gly Lys Arg Val Trp
                485                 490                 495
Leu Gln Pro Lys Val Val Ile Glu Val Thr Tyr Gln Glu Ile Gln Lys
                500                 505                 510
```

```
Ser Pro Lys Tyr Arg Ser Gly Phe Ala Leu Arg Phe Pro Arg Phe Val
        515                 520                 525

Ala Leu Arg Asp Asp Lys Gly Pro Glu Asp Ala Arg Thr Ile Glu Arg
    530                 535                 540

Ile Ala Gln Leu Tyr Glu Leu Gln Glu Lys Met Lys Gly Lys Val Glu
545                 550                 555                 560

Ser

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctagtggatc tgatgcgtta tctgg                                        25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcgggactat tgttagacct tagc                                         24

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggccatgggt tatctggagc ttgctcaac                                    29

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcggatcctt agctttccac ttttctttca tc                                32

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggaccagaag atgcagctac aatagagaga                                   30

<210> SEQ ID NO 16
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 16
tctctctatt gtagctgcat cttctggtcc                                          30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggaccagaag atgcatctac aatagagaga                                          30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctctctatt gtagatgcat cttctggtcc                                          30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggaccagaag atgcacgtac aatagagaga                                          30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tctctctatt gtacgtgcat cttctggtcc                                          30

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
caatcctctg gagtcgacct gtaggaatgc aagcttggcg                               40

<210> SEQ ID NO 22
<211> LENGTH: 30
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 22
aggtcgactc cagaggattg ttgaccggcc                                    30

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cgccaagctt gcattcctac                                               20

<210> SEQ ID NO 24
<211> LENGTH: 88
<212> TYPE: PRT
<213> ORGANISM: Pyrobaculum aerophilum

<400> SEQUENCE: 24

His Arg His Pro Arg Val Val Ser Lys Met Glu Ala Asp Val Trp Phe
1               5                   10                  15

Val Pro Gln Val Val Ile Glu Val Ile Gly Ala Glu Ile Thr Leu Ser
            20                  25                  30

Pro Leu His Thr Cys Cys Leu Gly Ala Val Arg Pro Gly Val Gly Leu
        35                  40                  45

Ala Val Arg Phe Pro Arg Phe Thr Gly Arg Tyr Arg Ser Asp Lys Ser
    50                  55                  60

Pro Glu Gln Ala Thr Thr Val Ala Glu Met Leu Glu Leu Tyr Lys Arg
65                  70                  75                  80

Gln Lys Lys Val Val Gln Pro Glu
                85

<210> SEQ ID NO 25
<211> LENGTH: 92
<212> TYPE: PRT
<213> ORGANISM: Desufurolobus ambivalens

<400> SEQUENCE: 25

Thr Pro His Pro Arg Val Val Ser Thr Met Val Pro Asp Val Trp Leu
1               5                   10                  15

Thr Pro Ala Leu Val Ala Glu Ile Ile Gly Ala Glu Ile Thr Ile Ser
            20                  25                  30

Pro Leu His Thr Cys Cys Lys Asp Gln Tyr Ala Glu Gly Gly Leu Ser
        35                  40                  45

Ile Arg Phe Pro Arg Phe Ile Arg Trp Arg Pro Asp Lys Ser Pro Glu
    50                  55                  60

Asp Ala Thr Thr Asn Arg Glu Ile Leu Glu Met Tyr Lys Ser Gln Leu
65                  70                  75                  80

Lys Lys Ile Glu Glu Lys Pro Ser Asp Gln Ser Val
                85                  90

<210> SEQ ID NO 26
<211> LENGTH: 69
<212> TYPE: PRT
<213> ORGANISM: Archaeglobus fulgidus

<400> SEQUENCE: 26

```
Gln Gln Gly Lys Lys Val Glu Phe Ile Pro Lys Tyr Val Phe Glu Val
1               5                   10                  15

Ala Tyr Gln Glu Ile Gln Lys Ser Pro Lys Tyr Glu Ser Gly Tyr Ala
            20                  25                  30

Leu Arg Phe Pro Arg Phe Val Arg Leu Arg Asp Asp Lys Asp Val Asp
            35                  40                  45

Glu Ala Asp Thr Ile Glu Arg Val Glu Asn Leu Tyr Lys Leu Gln Phe
    50                  55                  60

Glu Val Lys Arg Gln
65

<210> SEQ ID NO 27
<211> LENGTH: 69
<212> TYPE: PRT
<213> ORGANISM: Methanobacterium thermoautotrophicum

<400> SEQUENCE: 27

Arg Lys Gly Arg Lys Leu Leu Val Arg Pro Glu Ile Ile Leu Glu Val
1               5                   10                  15

Ala Tyr Ser Glu Ile Val Lys Ser Pro Glu Tyr Glu Ser Gly Tyr Ser
            20                  25                  30

Leu Arg Phe Pro Val Val Lys Arg Ile Arg Asp Asp Leu Cys Leu Asp
            35                  40                  45

Asp Val Asp Thr Val Gly Arg Ile Glu Ser Leu Phe Gln Ser Gly Gln
    50                  55                  60

Pro Asp Gln Pro Gly
65

<210> SEQ ID NO 28
<211> LENGTH: 67
<212> TYPE: PRT
<213> ORGANISM: Methanococcus jannaschii

<400> SEQUENCE: 28

Asp Leu Gly Glu Glu Val Glu Val Pro Lys Ile Val Ile Glu Val
1               5                   10                  15

Ala Tyr Glu Glu Ile Gln Lys Ser Asp Lys Tyr Pro Cys Gly Tyr Ala
            20                  25                  30

Leu Arg Phe Pro Arg Val Val Arg Phe Arg Phe Asp Lys Gly Val Asn
            35                  40                  45

Glu Ile Asn Thr Ile Glu Asp Val Glu Arg Ile Tyr Glu Ile Gln Arg
    50                  55                  60

Gly Arg Lys
65

<210> SEQ ID NO 29
<211> LENGTH: 70
<212> TYPE: PRT
<213> ORGANISM: Thermococcus kodakaraensis

<400> SEQUENCE: 29

Gln Glu Gly Lys Phe Val Glu Ile Glu Pro Lys Phe Val Ile Glu Val
1               5                   10                  15

Thr Tyr Gln Glu Ile Gln Lys Ser Pro Lys Tyr Lys Ser Gly Phe Ala
            20                  25                  30

Leu Arg Phe Pro Arg Tyr Val Ala Leu Arg Glu Asp Lys Ser Pro Glu
            35                  40                  45

Glu Ala Asp Thr Ile Glu Arg Val Ala Glu Leu Tyr Glu Leu Gln Glu
    50                  55                  60
```

```
Arg Phe Lys Ala Lys Lys
 65                  70

<210> SEQ ID NO 30
<211> LENGTH: 70
<212> TYPE: PRT
<213> ORGANISM: Pyrococcus abyssi

<400> SEQUENCE: 30

Glu Glu Gly Lys Arg Val Trp Ile Gln Pro Lys Val Val Ile Glu Val
  1               5                  10                  15

Thr Tyr Gln Glu Ile Gln Lys Ser Pro Lys Tyr Arg Ser Gly Phe Ala
             20                  25                  30

Leu Arg Phe Pro Arg Tyr Val Ala Leu Arg Glu Asp Lys Gly Pro Glu
         35                  40                  45

Asp Ala Asp Thr Ile Glu Arg Ile Ala Gln Leu Tyr Glu Leu Gln Glu
     50                  55                  60

Arg Met Lys Gly Lys Val
 65                  70

<210> SEQ ID NO 31
<211> LENGTH: 72
<212> TYPE: PRT
<213> ORGANISM: Pyrococcus furiosus

<400> SEQUENCE: 31

Glu Glu Gly Lys Arg Val Trp Leu Gln Pro Lys Val Val Ile Glu Val
  1               5                  10                  15

Thr Tyr Gln Glu Ile Gln Lys Ser Pro Lys Tyr Arg Ser Gly Phe Ala
             20                  25                  30

Leu Arg Phe Pro Arg Phe Val Ala Leu Arg Asp Asp Lys Gly Pro Glu
         35                  40                  45

Asp Ala Asp Thr Ile Glu Arg Ile Ala Gln Leu Tyr Glu Leu Gln Glu
     50                  55                  60

Lys Met Lys Gly Lys Val Glu Ser
 65                  70

<210> SEQ ID NO 32
<211> LENGTH: 101
<212> TYPE: PRT
<213> ORGANISM: Homo sapiens

<400> SEQUENCE: 32

Ser Pro Arg Pro Tyr Val Arg Ile Asp Gly Ala Val Ile Pro Asp His
  1               5                  10                  15

Trp Leu Asp Pro Ser Ala Val Trp Glu Val Lys Cys Ala Asp Leu Ser
             20                  25                  30

Leu Ser Pro Ile Tyr Pro Ala Ala Arg Gly Leu Val Asp Ser Asp Lys
         35                  40                  45

Gly Ile Ser Leu Arg Phe Pro Arg Phe Ile Arg Val Arg Glu Asp Lys
     50                  55                  60

Gln Pro Glu Gln Ala Thr Thr Ser Ala Gln Val Ala Cys Leu Tyr Arg
 65                  70                  75                  80

Lys Gln Ser Gln Ile Gln Asn Gln Gln Gly Glu Asp Ser Gly Ser Asp
                 85                  90                  95

Pro Glu Asp Thr Tyr
                100
```

```
<210> SEQ ID NO 33
<211> LENGTH: 85
<212> TYPE: PRT
<213> ORGANISM: Saccharomyces cerevisiae

<400> SEQUENCE: 33

Gly Pro Lys Ala Thr Phe Val Phe Asp Ser Ser Ala Glu Pro Asp Val
1               5                   10                  15

Trp Phe Glu Pro Thr Thr Leu Phe Glu Val Leu Thr Ala Asp Leu Ser
            20                  25                  30

Leu Ser Pro Ile Tyr Lys Ala Gly Ser Ala Thr Phe Asp Lys Gly Val
        35                  40                  45

Ser Leu Arg Phe Pro Arg Phe Leu Arg Ile Arg Glu Asp Lys Gly Val
    50                  55                  60

Glu Asp Ala Thr Ser Ser Asp Gln Ile Val Glu Leu Tyr Glu Asn Gln
65                  70                  75                  80

Ser His Met Gln Asn
                85
```